(12) United States Patent
Kovar

(10) Patent No.: US 10,588,972 B2
(45) Date of Patent: Mar. 17, 2020

(54) PHTHALOCYANINE PROBES AND USES THEREOF

(71) Applicant: LI-COR, INC., Lincoln, NE (US)

(72) Inventor: Joy L. Kovar, Lincoln, NE (US)

(73) Assignee: LI-COR, INC., Lincoln, NE (US)

( * ) Notice: Subject to any disclaimer, the term of this patent is extended or adjusted under 35 U.S.C. 154(b) by 209 days.

(21) Appl. No.: 14/728,304

(22) Filed: Jun. 2, 2015

(65) Prior Publication Data

US 2015/0374819 A1 Dec. 31, 2015

Related U.S. Application Data

(60) Provisional application No. 62/006,790, filed on Jun. 2, 2014, provisional application No. 62/017,165, filed on Jun. 25, 2014, provisional application No. 62/066,807, filed on Oct. 21, 2014, provisional application No. 62/082,052, filed on Nov. 19, 2014.

(51) Int. Cl.

| A61K 49/00 | (2006.01) |
|---|---|
| A61K 41/00 | (2020.01) |
| A61M 1/36 | (2006.01) |
| A61K 51/04 | (2006.01) |
| A61K 51/08 | (2006.01) |
| A61K 47/64 | (2017.01) |
| A61K 47/68 | (2017.01) |
| A61N 5/06 | (2006.01) |

(52) U.S. Cl.
CPC ...... *A61K 41/0071* (2013.01); *A61K 41/0009* (2013.01); *A61K 47/64* (2017.08); *A61K 47/642* (2017.08); *A61K 47/6415* (2017.08); *A61K 47/6849* (2017.08); *A61K 49/005* (2013.01); *A61K 49/0032* (2013.01); *A61K 51/0446* (2013.01); *A61K 51/0497* (2013.01); *A61K 51/082* (2013.01); *A61K 51/083* (2013.01); *A61K 51/088* (2013.01); *A61M 1/3618* (2014.02); *A61M 1/3683* (2014.02); *A61M 1/3686* (2014.02); *A61N 5/062* (2013.01); *A61K 49/0036* (2013.01); *A61N 2005/0658* (2013.01)

(58) Field of Classification Search
None
See application file for complete search history.

(56) References Cited

U.S. PATENT DOCUMENTS

| 6,995,274 B2 | 2/2006 | Lugade et al. |
|---|---|---|
| 7,005,518 B2 | 2/2006 | Peng et al. |
| 7,504,089 B2 | 3/2009 | Lugade et al. |
| 7,597,878 B2 | 10/2009 | Kovar et al. |
| 8,133,482 B2 | 3/2012 | Zheng et al. |
| 8,227,621 B2 | 7/2012 | Peng et al. |
| 8,303,936 B2 | 11/2012 | Draney et al. |
| 8,524,239 B2 * | 9/2013 | Kobayashi ............ C07K 16/30 424/178.1 |
| 8,889,835 B2 | 11/2014 | Govindan et al. |
| 9,358,306 B2 | 6/2016 | Bernardo et al. |
| 2002/0114793 A1 | 8/2002 | Edelson et al. |
| 2003/0139466 A1 | 7/2003 | Peritt et al. |
| 2005/0112131 A1 | 5/2005 | Pogue et al. |
| 2006/0134001 A1 | 6/2006 | Frangioni |
| 2006/0204443 A1 | 9/2006 | Kobayashi et al. |
| 2008/0081785 A1 | 4/2008 | Stewart et al. |
| 2008/0193431 A1 | 8/2008 | Zheng et al. |
| 2009/0156976 A1 | 6/2009 | Korbling et al. |
| 2010/0135902 A1 | 6/2010 | Roberts et al. |
| 2010/0215575 A1 * | 8/2010 | O'Neill ............... A61K 38/17 424/1.69 |
| 2010/0216226 A1 | 8/2010 | Hyde et al. |
| 2012/0010557 A1 | 1/2012 | Heger |
| 2012/0010558 A1 | 1/2012 | Kobayashi et al. |
| 2013/0039860 A1 | 2/2013 | Cheung |
| 2013/0116408 A1 | 5/2013 | De Los Pinos |
| 2013/0131423 A1 | 5/2013 | Wang et al. |
| 2013/0195760 A1 | 8/2013 | Olson |
| 2013/0287688 A1 | 10/2013 | Jain et al. |
| 2013/0302257 A1 | 11/2013 | Minko et al. |
| 2013/0336995 A1 | 12/2013 | Kobayashi et al. |
| 2014/0120119 A1 | 5/2014 | Kobayashi et al. |
| 2014/0161725 A1 | 6/2014 | Morse et al. |
| 2015/0343060 A1 | 12/2015 | Kovar et al. |
| 2015/0343084 A1 | 12/2015 | Dilley |
| 2016/0228568 A1 | 8/2016 | de los Pinos et al. |

FOREIGN PATENT DOCUMENTS

| GB | 1306627.9 | * | 4/2013 |
|---|---|---|---|
| WO | 2000/062807 A1 | | 10/2000 |
| WO | 2003/032900 A2 | | 4/2003 |

(Continued)

OTHER PUBLICATIONS

Mitsuanga et al. (Bioconj. Chem. 2012, 21, 604-609; see p. 1-10).*
Kovar et al. (Proc. of SPIE 2009 vol. 7190 71900N-1 to 71900N-8).*
Peng et al. (Proc. SPIE 2006, 6097, 60970E1-60970E12).*
Kovar et al. AACR-NCI-EORTC International Conference: Molecular Targets and Cancer Therapeutics—Nov. 12-16, 2011; San Francisco, CA, abstract C4.*
Ye et al. (J. Med. Chem. 2006, 49, 2268-2275).*
Haigler et al. (PNAS, 1978, 75, 3317-3321).*

(Continued)

*Primary Examiner* — Michael G. Hartley
*Assistant Examiner* — Melissa J Perreira
(74) *Attorney, Agent, or Firm* — Kilpatrick Townsend & Stockton LLP

(57) ABSTRACT

The present invention relates to compositions and methods for destroying target cells in a patient using photodynamic therapy. In particular, the present invention provides a photosensitizing agent based on a small molecular weight (<50 kDa) protein or peptide or a small molecule that is conjugated to a phthalocyanine dye, such as IRDye® 700DX.

17 Claims, 17 Drawing Sheets

Specification includes a Sequence Listing.

(56) References Cited

FOREIGN PATENT DOCUMENTS

| WO | 2007/070680 A2 | 6/2007 | |
|---|---|---|---|
| WO | 2008/005942 A2 | 1/2008 | |
| WO | 2009/079024 A1 | 6/2009 | |
| WO | 2009/107139 A1 | 9/2009 | |
| WO | 2011/014726 A1 | 2/2011 | |
| WO | WO 2011123742 A1 * | 10/2011 | ......... A61K 49/0032 |
| WO | 2012/078877 A2 | 6/2012 | |
| WO | 2013/009475 A1 | 1/2013 | |
| WO | 2015187651 | 12/2015 | |
| WO | 2015187677 | 12/2015 | |

OTHER PUBLICATIONS

Kovar et al, "A systematic approach to the development of fluorescent contrast agents for optical imaging of mouse cancer models," Analytical Biochemistry 367 (2007) 1-12.

Mitsunaga et al., "Cancer cell-selective in vivo near infrared photoimmunotherapy targeting specific membrane molecules," Nature Medicine, Dec. 2011, 17(12):1685-1691.

Peng et al., "Phthalocyanine dye as an extremely photostable and highly fluorescent near-infrared labeling reagent," Proceedings of SPIE, vol. 6097, E1-12.

Peng et al., "Quenched near-infrared fluorescent peptide substrate for HIV-1 protease assay," Proceedings of SPIE, vol. 6097, F1-12.

Kircher et al., "A multimodal nanoparticle for preoperative magnetic resonance imaging and intraoperative optical brain tumor delineation", Cancer Res., vol. 63, Dec. 2003, pp. 8122-8125.

Reddy et al., "Vascular targeted nanoparticles for imaging and treatment of brain tumors", Clin. Cancer Res., vol. 12, No. 22, Nov. 2006, pp. 6677-6686.

Rhee et al., "Glycan-targeted virus-like nanoparticles for photodynamic therapy", Biomacromolecules, vol. 13, 2012, pp. 2333-2338.

Galanzha et al., "In Vivo Magnetic Enrichment Photoacoustic Diagnosis and Photothermal Purging of Infected Blood Using Multifunctional Gold and Magnetic Nanoparticles", PLoS One, vol. 7 Issue 9 e45557, 2012, pp. 1-19.

Heukers et al., "Nanobody-photosensitizer conjugates for targeted photodynamic therapy", Nanomedicine: Nanotechnology, Biology, and Medicine 10, 2014, pp. 1441-1451.

Sharman et al., Targeted Photodynamic Therapy Via Receptor Mediated Delivery Systems, Science Direct, Advanced Drug Delivery Reviews, Elsevier, 2004, pp. 53-76, vol. 56.

Nakajima et al., Improving the Efficacy of Photoimmunotherapy (PIT) Using a Cocktail of Antibody Conjugates in a Multiple Antigen Tumor Model, (Theranostics 2013, vol. 3, Issue 6, Ivyspring International.

Wicki et al., [Lys$^{40}$(Ahx-DTPA-$^{111}$In)NH$_2$]-Exendin-4 Is a Highly Efficient Radiotherapeutic for Glucagon-Like Peptide-1 Receptor-Targeted Therapy for Insulinoma, Clinical Cancer Research 2007; 13(12), Cancer Therapy: Preclinical, pp. 3696-3705 www.aacrjournals.org.

* cited by examiner

| FIG. 6A | FIG. 6B | FIG. 6C | FIG. 6D |
| --- | --- | --- | --- |
| Control A431 NI | Control A431 I | EGF-700DX A431 NI | EGF-700DX A431 I |
| 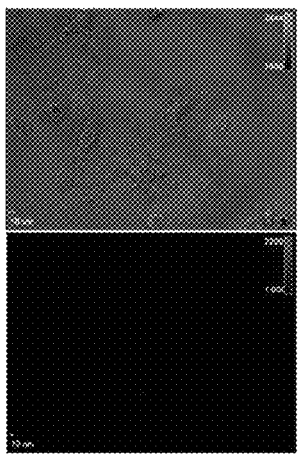 | 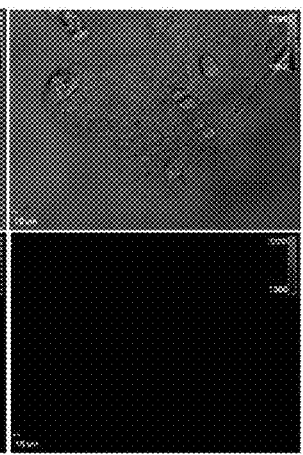 | 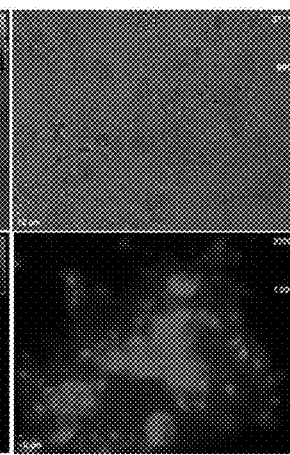 | 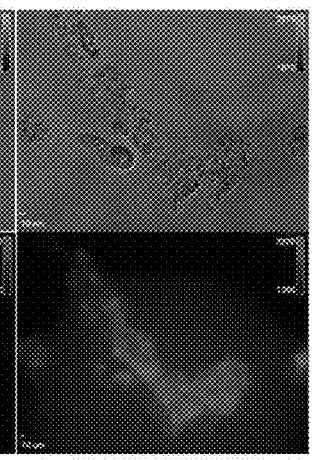 |
| 98.3% | 96.7% | 96.6% | 42.8% |
Cell Viability, %

FIG. 7A
FIG. 7B
DIC
700nm
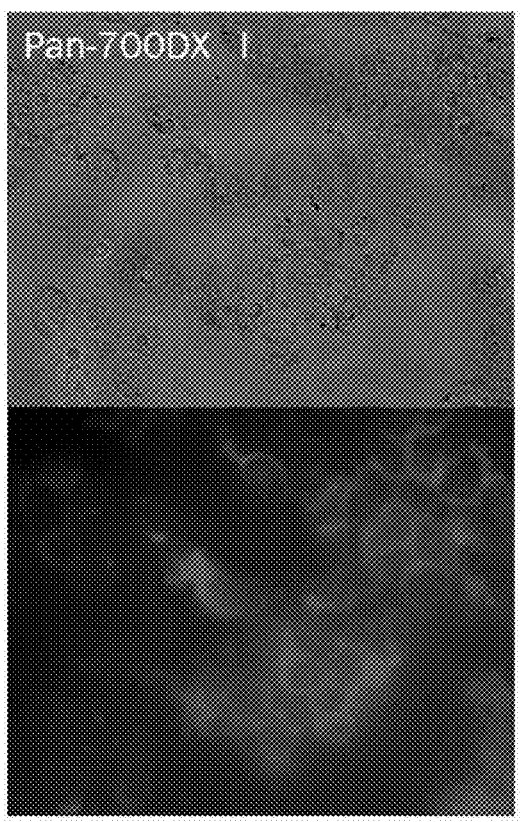
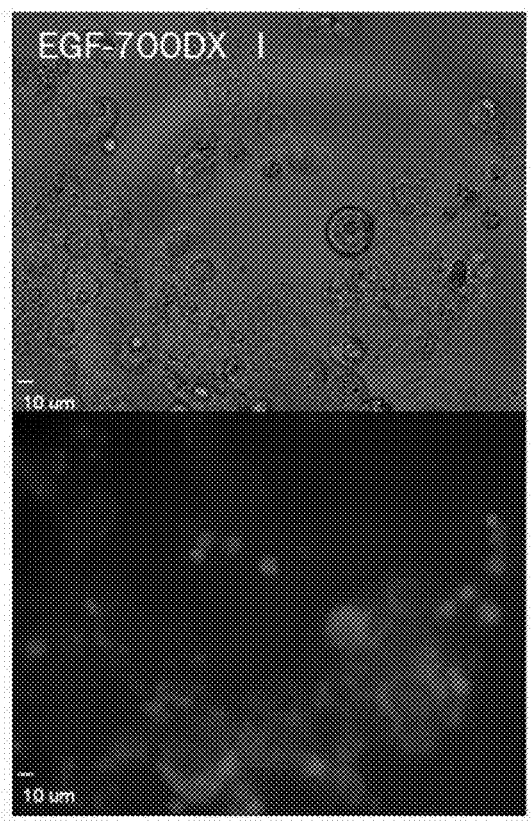

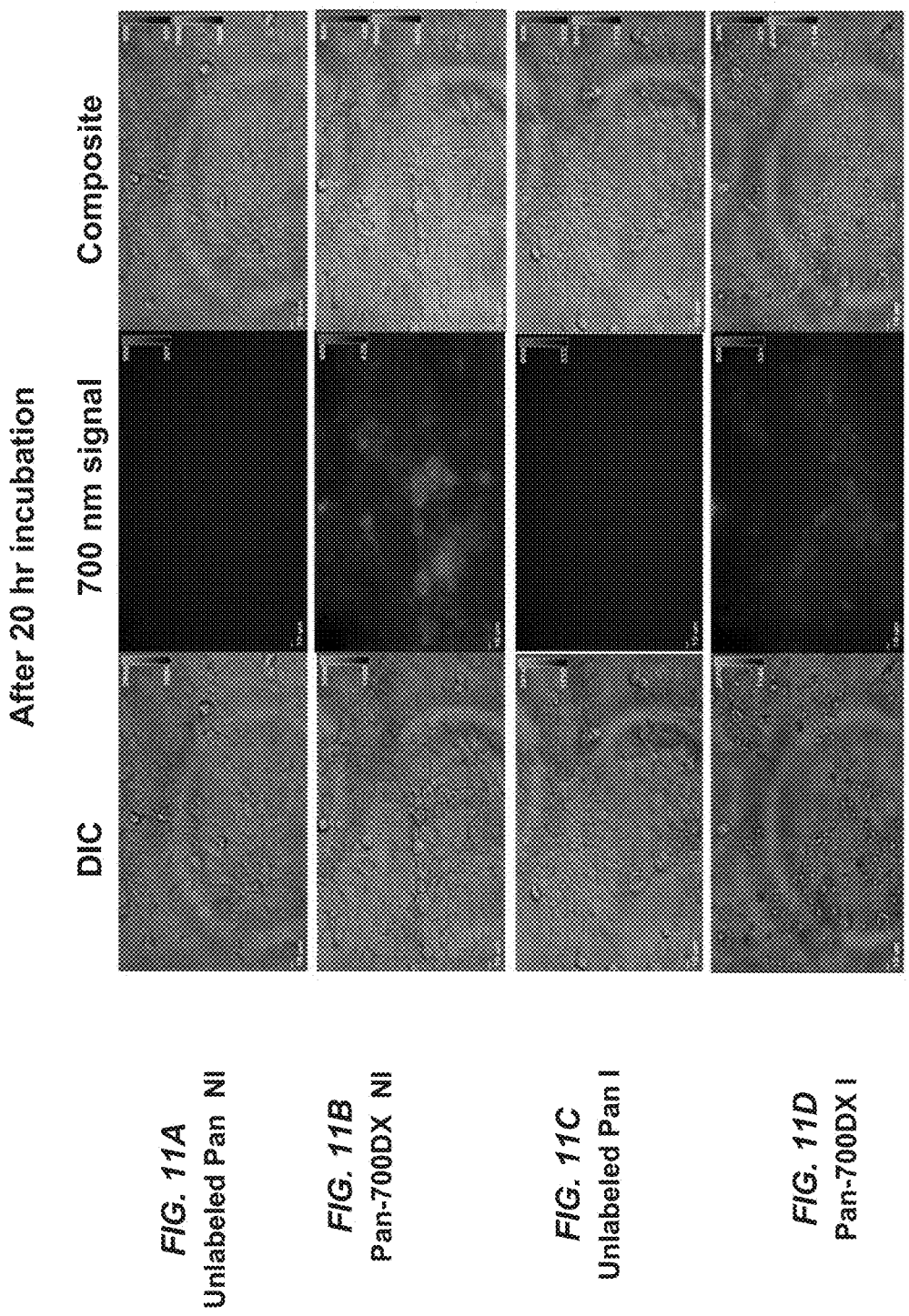
FIG. 11A Unlabeled Pan NI
FIG. 11B Pan-700DX NI
FIG. 11C Unlabeled Pan I
FIG. 11D Pan-700DX I

FIG. 11E

| Treatment | % | Cells/mL | VB-48 % necrotic | Annexin-V, % necrotic |
|---|---|---|---|---|
| Unlab pan  NI | 98.5 | $3.6 \times 10^6$ | 10 | 12 |
| Pan-700DX NI | 98.5 | $3.4 \times 10^6$ | 3 | 16 |
| Unlab pan  I | 97.4 | $3.6 \times 10^6$ | 12 | 21 |
| Pan-700DX I | 87.1 | $1.4 \times 10^6$ | 36 | 21 |

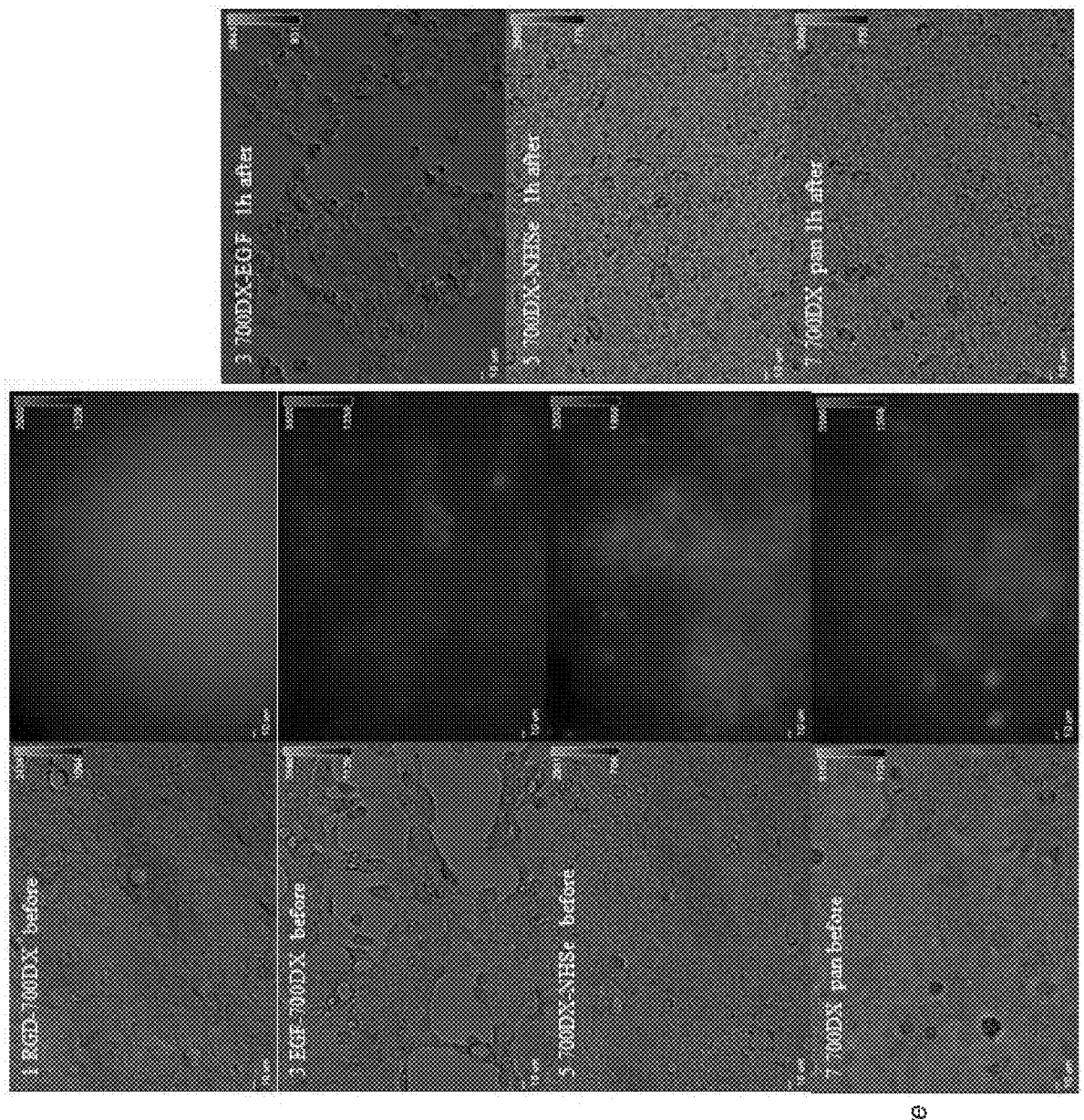
FIG. 13A 1 RGD-700DX before
FIG. 13B 3 EGF-700DX before
FIG. 13C 7 300DX-NHSe before
FIG. 13D Pan-700DX 700DX-Pan before
FIG. 13E 3 EGF-700DX 1 h after
FIG. 13F 5 700DX-NHSe 1 h after
FIG. 13G 7 700DX-Pan 1 h after

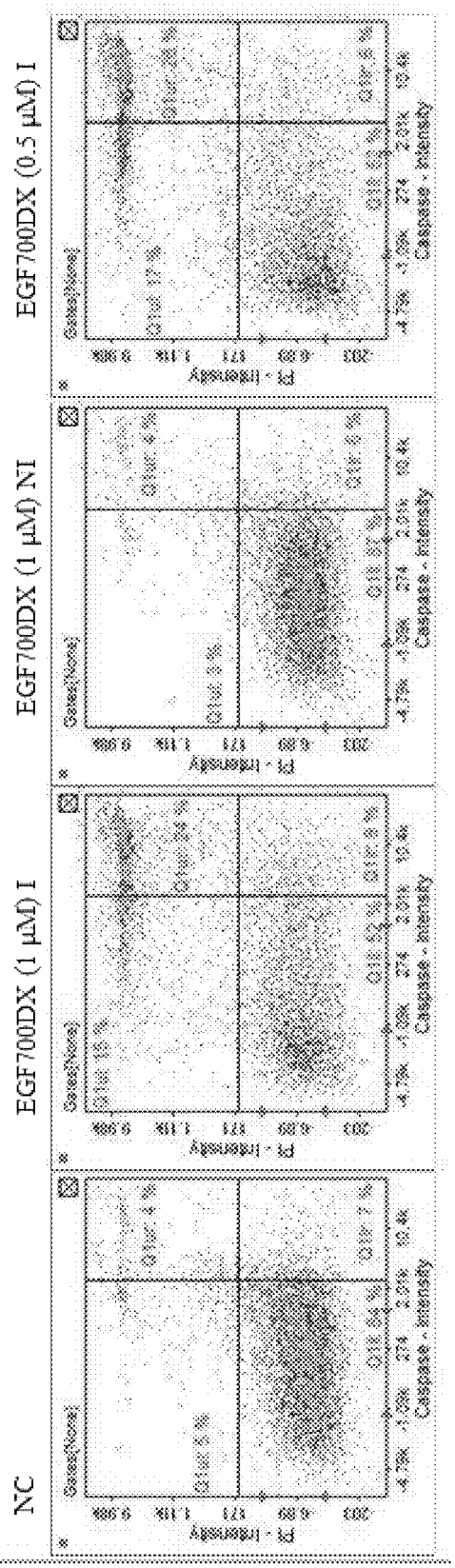
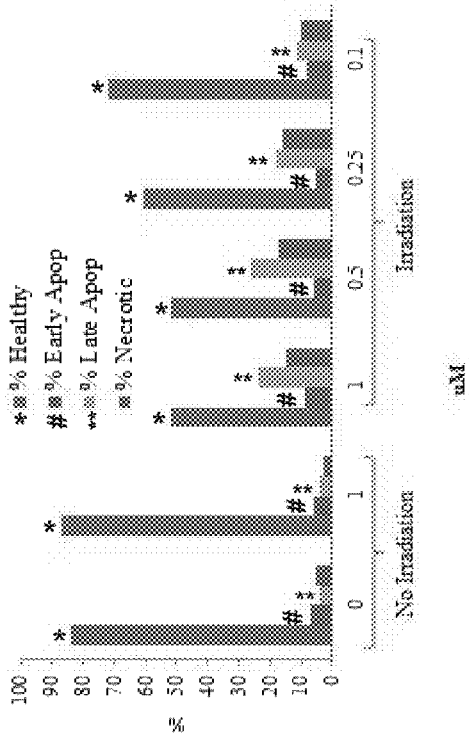
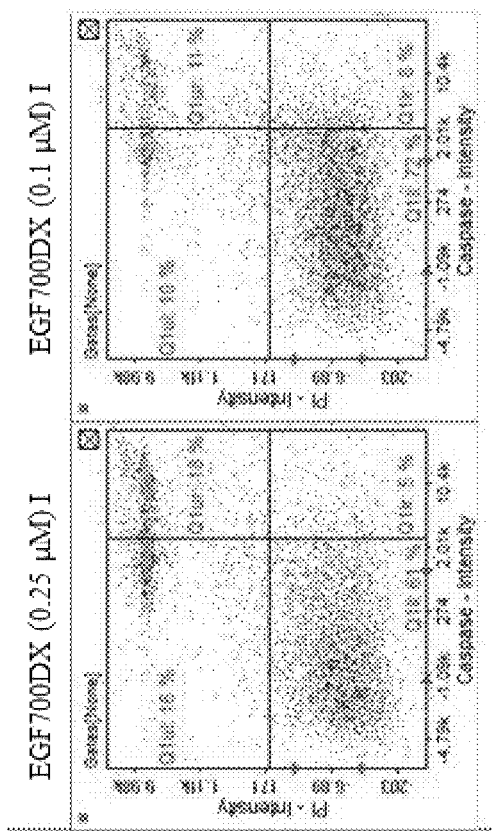
FIG. 15A  NC
FIG. 15B  EGF700DX (1 μM) I
FIG. 15C  EGF700DX (1 μM) NI
FIG. 15D  EGF700DX (0.5 μM) I
FIG. 15E  EGF700DX (0.25 μM) I
FIG. 15F  EGF700DX (0.1 μM) I
FIG. 15G  Caspase 3/7 Assay - EGF-700DX A431

SEQUENCE LISTING

<160> NUMBER OF SEQ ID NOS: 12

<210> SEQ ID NO 1
<211> LENGTH: 53
<212> TYPE: PRT
<213> ORGANISM: Artificial Sequence
<220> FEATURE:
<223> OTHER INFORMATION: Synthetic Epidermal growth factor

<400> SEQUENCE: 1

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 2
<211> LENGTH: 9
<212> TYPE: PRT
<213> ORGANISM: Artificial Sequence
<220> FEATURE:
<223> OTHER INFORMATION: Sytnthetic Construct, WP9QY, TNF - alpha
      Antagonist

<400> SEQUENCE: 2

Tyr Cys Trp Ser Gln Tyr Leu Cys Tyr
1               5

<210> SEQ ID NO 3
<211> LENGTH: 28
<212> TYPE: PRT
<213> ORGANISM: Artificial Sequence
<220> FEATURE:
<223> OTHER INFORMATION: Synthetic vasoactive intestinal peptide (VIP)

<400> SEQUENCE: 3

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 4
<211> LENGTH: 14
<212> TYPE: PRT
<213> ORGANISM: Bombina bombina
<220> FEATURE:
<221> NAME/KEY: VARIANT
<222> LOCATION: (1)..(1)
<223> OTHER INFORMATION: Xaa= Pyroglutamic acid

<400> SEQUENCE: 4

Xaa Gln Arg Leu Gly Asn Gln Trp Ala Val Gly His Leu Met
1               5                   10

<210> SEQ ID NO 5
<211> LENGTH: 11
<212> TYPE: PRT
<213> ORGANISM: Homo sapiens

<400> SEQUENCE: 5

Arg Pro Lys Pro Gln Gln Phe Phe Gly Leu Met
1               5                   10

<210> SEQ ID NO 6
<211> LENGTH: 15
<212> TYPE: PRT
<213> ORGANISM: Homo sapiens

<400> SEQUENCE: 6

Cys Phe Gly Ile Lys Gln Lys Asp Ile Asp Lys Asp Leu Val Ile
1               5                   10                  15

<210> SEQ ID NO 7
<211> LENGTH: 8
<212> TYPE: PRT
<213> ORGANISM: Artificial Sequence
<220> FEATURE:
<223> OTHER INFORMATION: Sytnthetic Construct, Octreotide
<220> FEATURE:
<221> NAME/KEY: VARIANT
<222> LOCATION: (1)..(1)
<223> OTHER INFORMATION: Xaa = D-Phenylalanine
<220> FEATURE:
<221> NAME/KEY: VARIANT
<222> LOCATION: (4)..(4)
<223> OTHER INFORMATION: Xaa = D-Tryptophan

<400> SEQUENCE: 7

Xaa Cys Phe Xaa Lys Thr Cys Thr
1               5

<210> SEQ ID NO 8
<211> LENGTH: 39
<212> TYPE: PRT
<213> ORGANISM: Artificial Sequence
<220> FEATURE:
<223> OTHER INFORMATION: Synthetic Construct, Exendin-4

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 9
<211> LENGTH: 13
<212> TYPE: PRT
<213> ORGANISM: Blarina brevicauda

<400> SEQUENCE: 9

Lys Glu Phe Leu His Pro Ser Lys Val Asp Leu Pro Arg
1               5                   10

<210> SEQ ID NO 10
<211> LENGTH: 27
<212> TYPE: PRT
<213> ORGANISM: Blarina brevicauda

<400> SEQUENCE: 10

Glu Gly Lys Leu Ser Ser Asn Asp Thr Glu Gly Gly Leu Cys Lys Glu
1               5                   10                  15

Phe Leu His Pro Ser Lys Val Asp Leu Pro Arg
            20                  25

<210> SEQ ID NO 11

```
<211> LENGTH: 54
<212> TYPE: PRT
<213> ORGANISM: Blarina brevicauda

<400> SEQUENCE: 11

Asp Cys Ser Gln Asp Cys Ala Ala Cys Ser Ile Leu Ala Arg Pro Ala
1               5                   10                  15

Glu Leu Asn Thr Glu Thr Cys Ile Leu Glu Cys Glu Gly Lys Leu Ser
            20                  25                  30

Ser Asn Asp Thr Glu Gly Gly Leu Cys Lys Glu Phe Leu His Pro Ser
        35                  40                  45

Lys Val Asp Leu Pro Arg
    50

<210> SEQ ID NO 12
<211> LENGTH: 36
<212> TYPE: PRT
<213> ORGANISM: Leiurus quinquestriatus

<400> SEQUENCE: 12

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35
```

PHTHALOCYANINE PROBES AND USES THEREOF

CROSS-REFERENCE TO RELATED APPLICATIONS

This application claims priority to U.S. Provisional Patent Application Nos. 62/006,790, filed Jun. 2, 2014; 62/017,165, filed Jun. 25, 2014; 62/066,807, filed Oct. 21, 2014 and 62/082,052, filed Nov. 19, 2014, the teachings all of which are hereby incorporated by reference in their entireties for all purposes.

REFERENCE TO A SEQUENCE LISTING

The Sequence Listing written in file SequenceListing_85409-025720US-945078.txt, created on Jul. 7, 2015, 4,447 bytes, machine format IBM-PC, MS-Windows operating system, is hereby incorporated by reference in its entirety for all purposes.

BACKGROUND OF THE INVENTION

Photodynamic therapy is a treatment method that uses a photosensitizing agent and irradiating light to destroy cells of interest in the body. When the photosensitizer is exposed to a specific wavelength of light, it produces a cytotoxic reactive oxygen species that can induce apoptosis, necrosis and/or autophagy of nearby cells.

Current photodynamic therapy methods rely on using antibodies or fragments thereof to localize the photosensitizing agent to the target cells. There is, however, a need for improved photosensitizing probes based on small molecule conjugates to induce apoptosis in target cells, e.g., diseased cells, in a subject using photodynamic therapy. The present invention satisfies this need and provides related advantages as well.

BRIEF SUMMARY OF THE INVENTION

In one embodiment, the present invention provides a method for inducing cytotoxicity, e.g., apoptosis in a subject having a disease or condition. The method includes (a) administering to the subject a therapeutically effective agent comprising a phthalocyanine dye such as IRDye® 700DX conjugated to a probe that specifically binds to a cell in the subject; and (b) irradiating the cell with an appropriate excitation light in an amount to effectively induce cell death. The phthalocyanine dye IRDye® 700DX conjugated to a probe is a compound of Formula Ia.

In some aspects, the disease or condition is selected from the group of a vascular disease, cancer, infection due to a bacterial biofilm, an antibiotic-resistant wound infection, actinic keratosis, rosacea, acne, and psoriasis. The vascular disease can be wet age-related macular degeneration. In some instances, the cancer is selected from the group consisting of breast cancer, colorectal cancer, esophageal cancer, endobronchial cancer, high-grade dyslasia in Barrett's esophagus, lung cancer, prostate cancer, cervical cancer, ovarian cancer, gastric cancer, pancreatic cancer, liver cancer, bladder cancer, brain cancer, head and neck cancer, neuroendocrine cancer, skin cancer, and combinations thereof.

In some aspects, the subject has a solid tumor or has had a solid tumor. The cell in the subject can be in the solid tumor, in the subject's blood, or at the site of metastasis.

In some instances, the appropriate excitation light has a wavelength of 660 to 740 nm, e.g., 660 nm, 670 nm, 680 nm, 690 nm, 700 nm, 710 nm, 720 nm, 730 nm, or 740 nm.

In some aspects, the probe is selected from the group of a ligand, peptide, small protein, small molecule, and combinations thereof. In some instances, the probe has a molecular weight of less than about 50 kDa. In other instances, the probe has a molecular weight of less than about 10 kDa. The ligand can be EGF. The peptide can be selected from the group of YC-27, cRGDfK, vasoactive intestinal peptide, gastrin-releasing peptide, neurotensin, AH111585, FPPRGD2, PK11195, SPARC, bombesin, neurotensin, substance P, somatostatin, cholecystokinin, glucagon-like peptide-1, neuropeptide Y, octreotide, DOTA-TOC, DOTA-TATE, exendin-4, RGD, analogs thereof, derivatives thereof, and combinations thereof. In some aspects, the peptide is selected from the group of soricidin, SOR-13 and SOR-C27. In other aspects, the small molecule is selected from the group of a VEGFR inhibitor, a TNFR1 inhibitor, a growth factor receptor inhibitor and combinations thereof. In some instances, the small molecule VEGFR inhibitor is selected from the group of pazopanib, semaxanib, axitinib, cabozantinib, aflibercept, brivanib, tivozanib, ramucirumab, motesanib, vatalanib, cediranib, and combinations thereof. Alternatively, the probe can be a member selected from the group of DTPA-octreotide, [Gluc-Lys]-TOCA, galacto-RGD, AH111585, RGD-K5, FPPRGD2, RP-527, BZH$_3$, [DTPA-Lys$^{40}$]-Exendin-4, and Tc-NT-X1. In some instances, the probe is a peptide ligand, an Affibody® or a derivative thereof.

In some aspects, the probe is conjugated to a radionuclide or has a radionuclide incorporated therein. The probe can also be conjugated to a fluorophore.

In some aspects, the administering of step (a) includes injecting the therapeutically effective agent, the phthalocyanine dye IRDye® 700DX conjugated to a probe into the subject's blood. In some aspects, the irradiating of step (b) comprises using a device comprising a near infrared (NIR) light emitting diode. The method described herein can also include administering an anticancer drug to the subject. The phthalocyanine dye IRDye® 700DX conjugated to a probe is a compound of Formula Ia.

In another embodiment, the present invention provides a method for treating a solid tumor in a subject having cancer. The method includes (a) administering to the subject a therapeutically effective agent comprising a phthalocyanine dye conjugated to a probe that specifically binds to a cell of the solid tumor; and (b) irradiating the cell with an appropriate excitation light in an amount to effectively reduce the size of the solid tumor.

In some aspects, the solid tumor is selected from the group of breast tumor, colorectal tumor, lung tumor, prostate tumor, ovarian tumor, gastric tumor, pancreatic tumor, liver tumor, bladder tumor, brain tumor, neuroendocrine tumor, and combinations thereof.

In some aspects, the phthalocyanine dye is IRDye® 700DX. In some instances, the appropriate excitation light has a wavelength of 660 to 740 nm, e.g., 660 nm, 670 nm, 680 nm, 690 nm, 700 nm, 710 nm, 720 nm, 730 nm, or 740 nm.

In some aspects, wherein the probe is selected from the group of a ligand, peptide, small protein, small molecule, and combinations thereof. In some instances, the probe has a molecular weight of less than about 50 kDa. In other instances, the probe has a molecular weight of less than about 10 kDa. The ligand can be EGF. The peptide can be selected from the group of YC-27, cRGDfK, vasoactive intestinal peptide, gastrin-releasing peptide, neurotensin, AH111585, FPPRGD2, PK11195, SPARC, bombesin, neurotensin, substance P, somatostatin, cholecystokinin, glucagon-like peptide-1, neuropeptide Y, octreotide, DOTA-TOC, DOTA-TATE, exendin-4, analogs thereof, derivatives thereof, and combinations thereof. In some aspects, the peptide is selected from the group of soricidin, SOR-13 and SOR-C27. In other aspects, the small molecule is selected from the group of a VEGFR inhibitor, a TNFR1 inhibitor, a growth factor receptor inhibitor and combinations thereof. In some instances, the small molecule VEGFR inhibitor is selected from the group of pazopanib, semaxanib, axitinib, cabozantinib, aflibercept, brivanib, tivozanib, ramucirumab, motesanib, vatalanib, cediranib, and combinations thereof. Alternatively, the probe can be a member selected from the group of DTPA-octreotide, [Gluc-Lys]-TOCA, galacto-RGD, AH111585, RGD-K5, FPPRGD2, RP-527, $BZH_3$, [DTPA-$Lys^{40}$]-Exendin-4, and Tc-NT-X1. In some instances, the probe is a peptide ligand, an Affibody® or a derivative thereof.

In some other aspects, the probe is conjugated to a radionuclide. The probe can be conjugated to a fluorophore.

In some aspects, the irradiating of step (b) comprises using a device comprising a near infrared (NIR) light emitting diode. The method described herein can also include administering an anticancer drug to the subject.

In yet another embodiment, the present invention provides a therapeutically effective composition comprising a phthalocyanine dye such as IRDye® 700DX conjugated to a probe that specifically binds to a cancer cell in a subject, wherein the probe has a molecular weight of less than about 50 kDa. In some aspects, the probe has a molecular weight of less than about 10 kDa.

The phthalocyanine dye IRDye® 700DX conjugated to a probe is a compound of Formula Ia. In some instances, the appropriate excitation light has a wavelength of 660 to 740 nm, e.g., 660 nm, 670 nm, 680 nm, 690 nm, 700 nm, 710 nm, 720 nm, 730 nm, or 740 nm.

In some aspects, wherein the probe is selected from the group of a ligand, peptide, small protein, small molecule, and combinations thereof. The ligand can be EGF. The peptide can be selected from the group of YC-27, cRGDfK, vasoactive intestinal peptide, gastrin-releasing peptide, neurotensin, AH111585, FPPRGD2, PK11195, SPARC, bombesin, neurotensin, substance P, somatostatin, cholecystokinin, glucagon-like peptide-1, neuropeptide Y, octreotide, DOTA-TOC, DOTA-TATE, exendin-4, analogs thereof, derivatives thereof, and combinations thereof. In some aspects, the peptide is selected from the group of soricidin, SOR-13 and SOR-C27. In other aspects, the small molecule is selected from the group of a VEGFR inhibitor, a TNFR1 inhibitor, a growth factor receptor inhibitor and combinations thereof. In some instances, the small molecule VEGFR inhibitor is selected from the group of pazopanib, semaxanib, axitinib, cabozantinib, aflibercept, brivanib, tivozanib, ramucirumab, motesanib, vatalanib, cediranib, and combinations thereof. Alternatively, the probe can be a member selected from the group of DTPA-octreotide, [Gluc-Lys]-TOCA, galacto-RGD, AH111585, RGD-K5, FPPRGD2, RP-527, $BZH_3$, [DTPA-$Lys^{40}$]-Exendin-4, and Tc-NT-X1. In some instances, the probe is a peptide ligand, an Affibody® or a derivative thereof.

In some aspects, the probe is conjugated to a radionuclide or has a radionuclide incorporated therein. The probe can be conjugated to a fluorophore.

Other objects, features, and advantages of the present invention will be apparent to one of skill in the art from the following detailed description and figures.

BRIEF DESCRIPTION OF THE DRAWINGS

FIG. 3A illustrates the stability of IRDye® 700DX carboxylate at room temperature at pH 2.1 to pH 8. FIG. 3B illustrates the stability of IRDye® 700DX carboxylate at 37° C. at pH 2 to pH 8.

In FIG. 4A, the marker spilled over into the ovalbumin lane and generated a visible marker ladder.

FIGS. 5A-C show three different cells.

FIGS. 6A-D show the cell viability of A431 cells following incubation with IRDye® 700DX-EGF and irradiation (24 $J/cm^2$). FIG. 6A shows control A431 cells that have not been irradiated. FIG. 6B shows control A431 cells that have irradiated. FIG. 6C shows A431 cells that were incubated with IRDye® 700DX-EGF without irradiation. FIG. 6D shows A431 cells that were incubated with IRDye® 700DX-EGF at 24 hours after irradiation. The top panel represents phase images (DIC images) of the cells. The lower panel represents images of fluorescence (at 700 nm) of the cells.

FIGS. 7A-B show the cell viability of A431 cells following incubation with different IRDye® 700DX-conjugates and irradiation (24 $J/cm^2$). FIG. 7A shows A431 cells that were incubated with IRDye® 700DX-panitumumab and irradiation. 62% of the cells were necrotic after irradiation. FIG. 7B shows A431 cells that were incubated with IRDye® 700DX-EGF and irradiation. 36% of the treated cells were necrotic. The top panel represents phase images (DIC images) of the cells. The lower panel represents images of fluorescence (at 700 nm) of the cells.

FIG. 8A shows a series of dorsal views of a nude mouse administered IRDye® 700DX at timepoints ranging from 5 minutes to 24 hours after administration of the dye. FIG. 8B shows a plot of total fluorescence in whole animal over the image capture timepoints.

FIG. 9A shows a series of ventral views of a nude mouse administered IRDye® 700DX at timepoints ranging from 5 minutes to 24 hours after administration of the dye. The white arrow indicates the location of the liver. FIG. 9B shows a plot of total fluorescence in the whole animal over the image capture timepoints.

In FIG. 10A, organs other than the liver and kidney show little to no signal at 24 hours after injection of IRDye® 700DX. FIG. 10B shows a longitudinal slice through the kidney (4 nmole dye). FIG. 10C shows a graph of the level of IRDye® 700DX detected in various organs at 24 hours after injection.

FIGS. 11A-11E shows the results after receiving optionally labeled-panitumumab with and without irradiation. FIG. 11A shows the cells administered unlabeled panitumumab and no irradiation. FIG. 11B shows cells administered panitumumab-700DX and no irradiation. FIG. 11C shows cells administered unlabeled panitumumab and irradiation. FIG. 11D shows cells administered panitumumab-700DX and irradiation. The left images are DIC images, the middle images are 700 nm images, and the right images are merged images. FIG. 11E shows results for cell number after treatment and % necrosis by several analyses of viability and vitality.

FIG. 12A shows the control or no probe. FIGS. 12B-12D show the cell morphology and presence of IRDye® 700DX in cells administered an IRDye® 700DX-panitumumab (Pan-700DX) probe or IRDye® 700DX-EGF (EGF-700DX) probe and irradiated for 10 min (32 J/cm$^2$). FIG. 12A shows a negative control cells that were not administered a probe and were irradiated. FIG. 12B shows a negative control cells that were administered EGF-700DX and not irradiated. FIG. 12C shows cells that received EGF-700DX and irradiation. FIG. 12D shows cells that received panitumumab-700DX and irradiation. The left images represent DIC images and the right images represent 700 nm images.

FIGS. 13A-13G shows the morphology of cells that received treatments 1, 3, 5 or 7 with the corresponding 700 nm image to illustrate how effective labeling was prior to irradiation.

FIGS. 15A-15G shows FACS analysis of caspase3/7 levels of cells treated with different amounts (dosages) of the EGF-700DX probe. FIG. 15A represents the negative control (NC). FIG. 15B shows cells treated with 1 µM EGF-700DX and irradiated. FIG. 15C shows cells treated with 1 µM EGF-700DX and not irradiated. FIG. 15D shows cells treated with 0.5 µM EGF-700DX and irradiated. FIG. 15E shows cells treated with 0.25 µM EGF-700DX and irradiated. FIG. 15F shows cells treated with 0.1 µM EGF-700DX and irradiated. FIG. 15G provides a graph of the caspase 3/7 data.

DETAILED DESCRIPTION OF THE INVENTION

I. Introduction

Figure 1:
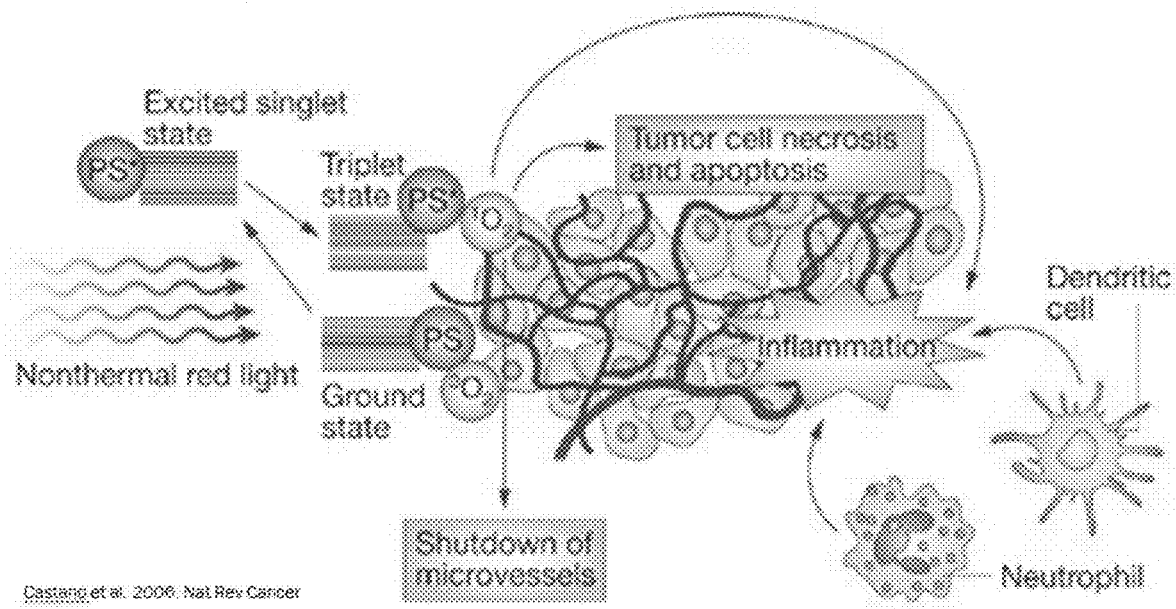
FIG. 1 provides a schematic diagram of photodynamic therapy as presented by Castano et al., *Nat Rev Cancer*, 2006, 6(7):535-545.

The present invention relates to compositions and methods for inducing targeted cell death in a subject with a disease or condition, such as vascular disease, cancer, skin conditions, skin infections, and other infections due to bacterial biofilms. More particularly, the invention involves the use of an IRDye® conjugated to probes (e.g., biomolecule) and irradiation to promote apoptosis and/or necrosis of specific target cells.

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "photodynamic therapy" or "PDT" includes a non-surgical treatment of cells, tissues or organs with both a non-toxic drug and photosensitizing irradiation to generate cytotoxic reactive oxygen species in situ, which can inactivate cells. For example, the molecular targeted therapy can utilize a target-specific photosensitizer agent, based on a near infrared (NIR) phthalocyanine dye, IRDye® 700DX, conjugated to a probe (e.g., biomolecule) that specifically bind to a target cell via a specific cell surface protein. For most application of PDT, the cytotoxic agent is produced by one of the two different processes called Type I or Type II PDT pathways. Type I generates radicals and Type II generates singlet oxygen. Both radicals and singlet oxygen cause oxidative destruction of tissues.

The term "cytotoxicity" includes the death of a cell or the process thereof due to exposing the cell to a toxin.

The term "cytotoxic agent" includes a substance that inhibits or prevents a cellular function and/or causes cell death or destruction. Non-limiting cytotoxic agents include radioactive isotopes; chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof.

The term "cancer" includes the physiological condition in mammals that is typically characterized by unregulated cell growth. Non-limiting examples of cancer include carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer The term "solid tumor" refers to an abnormal mass of cells that are either benign or malignant and usually do not contain cysts. Non-limiting examples of a solid tumor include glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

The term "phthalocyanine dye" includes a silicon phthalocyanine dye that are useful for conjugating to a probe, such as a protein. Non-limiting examples of a phthalocyanine dye, such as IRDye® 700DX are described in, e.g., U.S. Pat. No. 7,005,518, the disclosure of which is herein incorporated by reference in its entirety for all purposes.

The term "IRDye® 700DX" or "IR700" is a phthalocyanine dye, which when conjugated to a probe becomes a therapeutic effective agent. The IRDye® 700DX dye may have an NHS ester linkage to allow for conjugation to a probe. In some instances, the probe has a primary amine (e.g., an amino group) wherein the NHS ester of 700DX and the amino group of the probe react to form an amide bond, linking the probe to 700DX to form the therapeutic effective agent. The NHS ester IRDye® 700DX has the following structure:

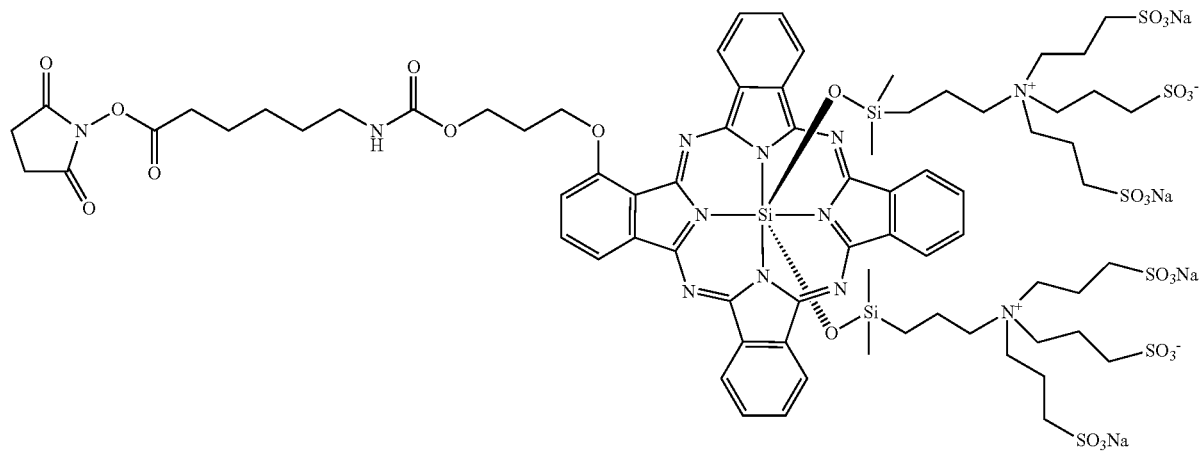

The dye is commercially available from LI-COR (Lincoln, Nebr.). Amino-reactive IRDye® 700DX is a relatively hydrophilic dye and can be covalently conjugated with a probe using the NHS ester of IRDye® 700DX. Other variations of IRDye 700DX are disclosed in U.S. Pat. No. 7,005,518 (incorporated herein by reference), and those too are useful in the present invention. The carboxylate derivative has the following name and structure, silicate(5-), bis[N— [3-[(hydroxy-.kappa.O)dimethylsilyl]propyl]-3-sulfo-N,N-bis(3-sulfopropyl)-1-propanaminiumato(4-)][6-[[[3-[(29H,31H-phthalocyanin-yl-.kappa.N29, .kappa.N30, .kappa.N31, .kappa.N32)oxy]propoxy]carbonyl]amino] hexanoato(3-)]-, sodium (1:5) CAS Registry Number: [1623074-46-3]:

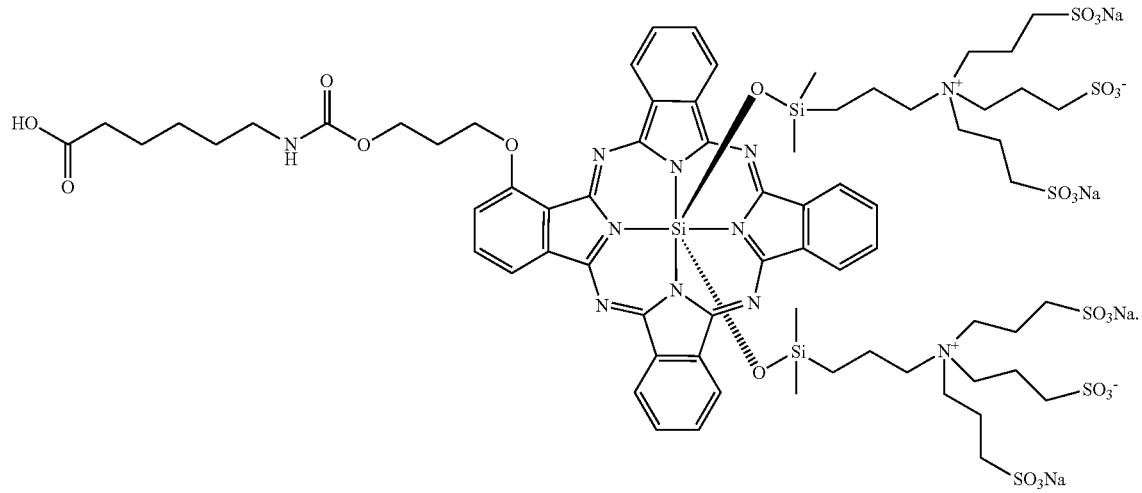

The term "cyanine dye" refers to a compound having two substituted or unsubstituted nitrogen-containing heterocyclic rings joined by an unsaturated bridge, such as a polymethine chain. Non-limiting examples of a cyanine dye, such as IRDye® 800CW are described in, e.g., U.S. Pat. Nos. 6,995,274; 7,504,089; 7,597,878; 8,227,621; 8,303,936; the disclosures of which are herein incorporated by reference in their entirety for all purposes.

The term "infrared fluorescent dye," "IR fluorescent dye" or "IR dye" refers to a dye having an absorption and emission wavelengths in the near-infrared spectrum of about 600-1000 nm. An infrared fluorescent dye can be detected using a near-infrared (NIR) fluorescence imaging system.

The term "probe" or "biomolecule" includes a natural or synthetic molecule for use in biological systems. Preferred biomolecules include a protein, a peptide, a small molecule, a ligand, an enzyme substrate, a hormone, an antibody, an antigen, a hapten, an avidin, a streptavidin, a carbohydrate, an oligosaccharide, a polysaccharide, a nucleic acid, a deoxy nucleic acid, a fragment of DNA, a fragment of RNA, nucleotide triphosphates, acyclo terminator triphosphates, and PNA.

The term "conjugated," "coupled" or "labeled" refers to linking of at least one chemical moiety to a protein by means of a suitable crosslinker capable of covalently binding the moiety to the protein.

The term "linking group" includes a moiety on the compound that is capable of chemically reacting with a functional group on a different material (e.g., probe) to form a linkage, such as a covalent linkage. See, e.g., R. Haughland, *The Handbook—A Guide to Fluorescent Probes and Labeling Technologies*, $9^{th}$ Edition, Molecular Probes, Inc. (1992). Typically, the linking group is an electrophile or nucleophile that can form a covalent linkage through exposure to the corresponding functional group that is a nucleophile or electrophile, respectively. Alternatively, the linking group is a photoactivatable group, and becomes chemically reactive only after illumination with light of an appropriate wavelength. Typically, the conjugation reaction between the dye bearing the linking group and the material to be conjugated with the dye "the probe" results in one or more atoms of the linking group being incorporated into a new linkage attaching the dye to the probe to form the therapeutic agent.

The term "linker" includes the atoms joining the dye to a probe.

The terms "treat" and "treatment" refer to both therapeutic treatment and prophylactic or preventative measures, wherein the object is to prevent or slow down (lessen) an undesired physiological change or disorder, such as the growth, development or spread of cancer. For example, beneficial or desired clinical results include, but are not limited to, alleviation of symptoms, diminishment of extent of disease, stabilized (i.e., not worsening) state of disease, delay or slowing of disease progression, amelioration of the disease state, and remission (whether partial or total), whether detectable or undetectable. "Treatment" can also mean prolonging survival as compared to expected survival if not receiving treatment. Those in need of treatment include those already with the condition or disorder as well as those prone to have or suspected to have the condition or disorder or those in which the condition or disorder is to be prevented.

The term "therapeutically effective amount" refers to an amount of a composition that alone, or together with an amount of an additional therapeutic agent(s) (such as a chemotherapeutic agent) is sufficient to achieve a desired effect in a subject, or in a cell, being treated with the composition. The effective amount of the therapeutic agent or composition (such as an IRDye® 700DX-probe) can be dependent on several factors, including, but not limited to the subject or cells being treated, the particular therapeutic agent, and the manner of administration of the therapeutic composition. For example, a therapeutically effective amount or concentration is sufficient to prevent advancement (such as metastasis), delay progression, or to cause regression of a disease, or which is capable of reducing symptoms caused by the disease, such as cancer. For instance, a therapeutically effective amount or concentration is sufficient to increase the survival time of a patient with a circulating tumor cell.

The term "subject," "patient," or "individual" typically refers to humans, but also to other animals including, e.g., other primates, rodents, canines, felines, equines, ovines, porcines, and the like.

III. Detailed Descriptions of Embodiments

A. Phthalocyanine Dye Conjugated to a Probe

Disclosed herein are targeted photosensitizing agents such as IRDye® 700DX-probes. Any targeting moiety such as an antigen, ligand, protein, peptide, carbohydrate, nucleic acids, or small molecule that specifically binds to the predetermined target cell can be used. The probe can be less than the molecular weight of an antibody. In some aspects, the probe is less than about 50 kDa, e.g., about 49 kDa, 45 kDa, 4-kDa, 35 kDa, 30 kDa, 25 kDa, 20 kDa, 15 kDa, 10 kDa, 5 kDa, 1 kDa, or less than 1 kDa. The probe can be less than about 10 kDa, e.g., 9 kDa, 8 kDa, 7 kDa, 6 kDa, 5 kDa, 4 kDa, 3 kDa, 2 kDa, 1 kDa, or less than 1 kDa.

B. Probes

The biomolecules useful for the present invention include small molecular weight proteins, ligands, peptides, cyclic peptides, small molecules, and analogs thereof that bind to the cell surface to the target cell. In some aspects, the biomolecule is EGF, YC-27, cRGDfK, vasoactive intestinal peptide, gastrin-releasing peptide, AH111585, FPPRGD2, PK11195, SPARC, bombesin, neurotensin, substance P, somatostatin, cholecystokinin, glucagon-like peptide-1, neuropeptide Y, octreotide, DOTA-TOC, DOTA-TATE, exendin-4, soricidin, SOR-13, SOR-C27, a small molecule VEGFR inhibitor, e.g., pazopanib, semaxanib, axitinib, cabozantinib, aflibercept, brivanib, tivozanib, ramucirumab, motesanib, vatalanib, cediranib, and combinations thereof, a small molecule TNF1R inhibitor, a growth factor receptor inhibitor, DTPA-octreotide, [Gluc-Lys]-TOCA, galacto-RGD, AH111585, RGD-K5, FPPRGD2, RP-527, $BZH_3$, [DTPA-$Lys^{40}$]-Exendin-4, Tc-NT-X1, analogs thereof or derivatives thereof.

1. Ligands

Epidermal growth factor or EGF is a 53-amino acid peptide that has a role in the growth, proliferation and differentiation of epidermal and epithelial tissues. It binds to its cognate receptor, the EGF receptor. The human EGF peptide is set forth in, e.g., Uniprot Accession No. P01133 or GenBank Accession Nos. NP_001171601, NP_001171602 and NP_001954. The human EGF mRNA (coding) sequence is set forth in, GenBank Accession Nos. NM_001178130, NM_001178131 and NM_001963. One skilled in the art will recognize that EGF is also known as pro-epidermal growth factor and urogastrone, and is cleaved to form the epidermal growth factor peptide. In some aspects, the EGF peptide ligand used in the present invention has the amino acid sequence of SEQ ID NO: 1 (NSDSECPLSHDGYCLHDGVCMYIEALDKYACNCVVGYIGER-CQYRDLKWWELR).

2. Peptides

Probes useful for the present invention include cyclic peptides. Peptides can be cyclized by a variety of methods such as formation of disulfides, sulfides and, especially, lactam bonds between carboxyl and amino functions of the N- and C-termini or amino acid side chains.

Cyclization can be obtained by any method known in the art, for example, through amide bond formation, by incorporating Glu, Asp, Lys, Orn, diamino butyric (Dab) acid, diaminopropionic (Dap) acid at various positions in the chain (—CO—NH or —NH—CO bonds). Backbone to backbone cyclization can also be obtained through incorporation of modified amino acids of the formulas H—N(CH$_2$)$_n$—COOH)—C(R)H—COOH or H—N((CH$_2$)$_n$—NH$_2$)—C(R)H—COOH, wherein n=1-4, and further wherein R is any natural or non-natural side chain of an amino acid. Cyclization can also be obtained via formation of S—S bonds through incorporation of two Cys residues. Additional side-chain to side chain cyclization can be obtained via formation of an interaction bond of the formula —(CH$_2$)$_n$—S—CH$_2$—CO—, wherein n=1 or 2, which is possible, for example, through incorporation of Cys or homoCys and reaction of its free SH group with, e.g., bromoacetylated Lys, Orn, Dab or Dap.

The terms "RGD-containing peptide" or "RGD peptide" are used herein interchangeably and mean a peptide containing the RGD sequence, also referred to as RGD motif. The term "RGD peptidomimetic" refers to compounds, particularly, non-peptidic compounds, that mimic peptides having the RGD motif.

The RGD-containing peptide may be a linear or cyclic peptide composed of 4-100, preferably 5-50, 5-30, 5-20 or, more preferably, 5-10 amino acid residues. In some aspects, the RGD peptide is composed of 4, 5, 6, 7, 9 or 25, most preferably 5 amino acid residues. The term "amino acid" includes the 20 naturally occurring amino acids as well as non-natural amino acids. Non-limiting examples of a non-natural amino acid include 4-aminobutyric acid (Abu), 2-aminoadipic acid, diaminopropionic (Dap) acid, hydroxylysine, homoserine, homovaline, homoleucine, norleucine (Nle), norvaline (Nva), ornithine (Orn), TIC, naphthylalanine (NaI), ring-methylated derivatives of Phe, halogenated derivatives of Phe or O-methyl-Tyr. Alternatively, an amino acid includes modified amino acids such as modifications that occur post-translationally in vivo, for example, hydroxyproline, phosphoserine and phosphothreonine; D-modification; N-alkylation, preferably N-methylation, of the peptide bond; acylation or alkylation of the amino terminal group or of the free amino group of Lys; esterification or amidation of the carboxy terminal group or of a free carboxy group of Asp or Glu; and esterification or etherification of the hydroxyl group of Ser or Tyr. Also, amino acid refers to both D-amino acids and L-amino acids.

VEGF receptor inhibitors include but are not limited to, VG3F (see, e.g., Goncalves et al., *J Pept Sci*, 14(6):767-72, 2008), VEGF-P3(NC) and VEGF-P3(CYC) (see, e.g., Vicari et al., *J Biol Chem*, 286:13612-13625, 2011).

Examples of inhibitors of tumor necrosis factor receptor 1 (TNFR1) include, but are not limited to, antibodies or fragments thereof, such as ATROSAB (see, e.g., Richter et al., *PloS One*, 8(8): e72156, 2013 and Zettlitz et al., *MAbs*, 2(6):639-647, 2010), IZI-06.1 (see, e.g., Kontermann et al., *J Immunother*, 31(3):225-34, 2008), anti-TNFR1 antagonists, or polypeptides disclosed in U.S. Patent Application Publication Nos. 2012/0107330 and 2012/0213787; small peptides, such as WP9QY (YCWSQYLCY) (SEQ ID NO: 2); see, e.g., Lohman and Isakson, The Faseb Journal, 28(1), Suppl. 669.8).

A TNFR1-selective antagonist can be a TNF-α mutant such as RlantTNF or PEG-RlantTNF (see, e.g., Shibata et al., *Cytokine*, 44(2):229-233, 2008 and Kitagaki et al., *J Altheroscler Thromb*, 19(1):36-46, 2012, respectfully).

YC-27 is a prostate specific membrane antigen-specific (PSMA-specific) small molecule. PSMA is also known as folate hydrolase I or glutamate carboxypeptidase II. See, e.g., U.S. Patent Application Publication No. 2012/0009121, Chen et al., *Biochem Biophys Res Commun*, 390(3):624-629, 2009 and Kovar et al., *Prostate Cancer*, 2014, article ID 104248, 10 pages.

Vasoactive intestinal peptide (VIP) is a brain/gut hormone that is located in neuronal cell bodies of the CNS, digestive, respiratory and urogenital tracts, exocrine glands, thyroid glands and adrenal glands. The human VIP peptide is set forth in, e.g., Uniprot Accession No. P01282 or GenBank Accession Nos. NP_003372 and NP_919416. The human VIP mRNA (coding) sequence is set forth in, GenBank Accession Nos. NM_003381 and NM_194435. One skilled in the art will recognize that VIP is also known as vasoactive intestinal polypeptide and that the peptide can be cleaved into three chains, e.g., intestinal peptide PHV-42 (peptide histidine valine 42), intestinal peptide PHM-27 (peptide histidine methioninamide 27) and a vasoactive intestinal peptide of 27 amino acids in length. In some aspects, the vasoactive intestinal peptide used in the present invention has the amino acid sequence of SEQ ID NO: 3 (HSDAVFTDNYTRLRKQMAVKKYLNSILN). VIP analogs includes [Lys$^{15}$, Arg$^{16}$, Leu$^{27}$]-VIP/GRF, RO 25-1553, and $^{18}$F-labeled-Arg$^{15}$-Arg$^{21}$-VIP.

Gastrin-releasing peptide or GRP is a neuropeptide that is generated, along with the 10-amino acid neuromedin C, following cleavage of a signal peptide from its 148-amino acid preproprotein. Gastrin-releasing peptide regulates numerous functions of the gastrointestinal and central nervous systems, including stimulating gastrin release. The human GRP peptide is set forth in, e.g., Uniprot Accession No. P07492 or GenBank Accession No. NP_001012530. The human GRP mRNA (coding) sequence is set forth in, GenBank Accession No. NM_001012512.

Neurotensin or NTS is a 13 amino acid neuropeptide that is generated following cleavage of the neurotensin/neuromedin N precursor. Neurotensin controls numerous functions of the central nervous system including smooth muscle contraction. The human neurotensin peptide is set forth in, e.g., Uniprot Accession No. P30990 or GenBank Accession No. NP_006174. The human neurotensin mRNA (coding) sequence is set forth in, GenBank Accession No. NM_006183.

AH111585 or fluciclatide is small cyclic peptide containing the RGD (arginine-glycine-aspartic acid) tri-peptide. It specifically binds to αVβ3 and αVβ5 integrins.

Cilengitide is small cyclic RGD peptide (e.g., cyclo (RGDfV) inhibitor of αVβ3 and αVβ5 integrins. The chemical structure of cilengitide is cyclo(Arg-Gly-Asp-D-Phe-Val) or cyclo(L-arginylglycyl-L-alpha-aspartyl-D-phenylalanyl-N-methyl-L-valyl).

Cyclo (RGDfK) or c(RGDfK) is a cyclic pentapeptide having the amino acid structure cyclo(Arg-Gly-Asp-D-Phe-Lys) or the chemical structure 2-[(2S,5R,8S,11S)-8-(4-aminobutyl)-5-benzyl-11-[3-(diaminomethylideneamino)propyl]-3,6,9,12,15-pentaoxo-1,4,7,10,13-pentazacyclopentadec-2-yl]acetic acid.

FPPRGD2 is a PEGylated dimeric RGD (arginine-glycine-asparate) peptide that repeating cyclic pentapeptide (Phe-Pro-Pro-Arg-Gly-Asp) units connected by glutamates. The peptide specifically binds to αVβ3 integrin.

Bombesin is 14-amino acid peptide with the amino acid sequence set forth in SEQ ID NO: 4 (Pyr-Gln-Arg-Leu-Gly-Asn-Gln-Trp-Ala-Val-Gly-His-Leu-Met-NH$_2$). Analogs of bombesin peptide include [Gly-Gly-Gly]-bombesin and d-Tyr6, betaAla$^{11}$, Phe$^{13}$, Nle$^{14}$]-bombesin.

The small molecule PK-11195 is an isoquinoline carboxamide that selectively binds to the peripheral benzodiazepine receptor. PK-11195 can act as a GABA-A antagonist. One skilled in the art will recognize that PK-11195 is also known as 1-(2-chlorophenyl)-N-methyl-N-(1-methylpropyl)-1-isoquinoline carboxamide.

Substance P is an undecapeptide belong to the tachykinins neuropeptide family. The human protachykinin-1 proprotein is set forth in, e.g., Uniprot Accession No. P20366 or GenBank Accession Nos. NP_003173, NP_054702, NP_054703 and NP_054704. The human protachykinin-1 mRNA (coding) sequence is set forth in, GenBank Accession Nos. NM_003182, NM_013996, NM_013997, and NM_013998. One skilled in the art recognizes that protachykinin-1 is cleaved to form 5 peptides including substance P, neurokinin A, neuromedin L, substance K and neuropeptide K. The amino acid sequence of substance P is set forth in SEQ ID NO: 5 (RPKPQQFFGLM).

Secreted protein acidic and rich in cysteine (SPARC) which is also known as osteonectin and BM-40 is a non-structural matrixcelluar 32-kDa glycoprotein. The protein can be used to identify infiltrating breast carcinoma, cancer cells expressing hypoxia and acidity markers, such as HIF2α and embryo-chondrocyte expressed gene 1, hepatocellular carcinoma, gastric carcinoma, bone metastasis of prostate cancer, cancer tissue hypoxia and acidity, bladder cancer, and lung carcinomas. The human SPARC preprotein is set forth in, e.g., Uniprot Accession No. P09486 or GenBank Accession No. NP_003109. The human SPARC mRNA (coding) sequence is set forth in, GenBank Accession No. NM_003118. The SPARC protein can be cleaved to form the SPARC peptide having the amino acid sequence set forth in SEQ ID NO: 6 (CFGIKQKDIDKDLVI).

Somatostatin is a peptide hormone that can regulate the endocrine system. The peptide can be a cyclic tetradecapeptide. The somatostatin peptide is generated by alternative cleavage of the preproprotein into a 14-amino acid peptide and a 28-amino acid peptide. The human somatostatin preprotein is set forth in, e.g., Uniprot Accession No. P61278 or GenBank Accession No. NP_001039. The human somatostatin mRNA (coding) sequence is set forth in, GenBank Accession No. NM_001048. One skilled in the art will recognize that somatostatin is also known as growth hormone release-inhibiting factor, growth hormone-inhibiting hormone, GHIH, somatotropin release-inhibiting factor, SRIF, somatotropin release-inhibiting hormone, SRIH, somatostatin-28 or somatostatin-14. Somatostatin analogs include, but are not limited to, octreotide, lanreotide, vapreotide, octapeptide BIM 23014 (SR lanreotide), slow-release form of octreotide (Sandostatin LAR), SOM230 (Novartis, Basel), BIM 23244 (Biomeasure, Milford, Mass.). Radiolabeled somatostatin peptides, such as $^{125}$I- or 123I-[Tyr3]octreotide, 110In-DTPA-[d=Phe1]octreotide (octreoscan), $^{111}$In-DOTA-lanreotide, $^{99m}$Tc-P829, $^{90}$Y-DOTA-Tyr3-octreotide ($^{90}$Y-DOTATOC), and DOTA-[1-NaI$_3$]-octreotide (DOTANOC) are also useful in the present invention.

Cholecystokinin is a peptide hormone that regulates the digestion of fat and protein by the gastrointestinal system. Cholecystokinin peptides are generated from alternative cleavage of the cholecystokinin proprotein, preprocholecystokinin. Cholecystokinin peptides include cholecystokinin-58, holecystokinin-58 desnonopeptide, cholecystokinin-39, cholecystokinin-33, cholecystokinin-25, cholecystokinin-18, cholecystokinin-12, cholecystokinin-8, cholecystokinin-7, cholecystokinin-5 The human cholecystokinin preprotein is set forth in, e.g., Uniprot Accession No. P06307 or GenBank Accession No. NP_000720. The human cholecystokinin mRNA (coding) sequence is set forth in, GenBank Accession No. NM_000729. In some aspects, the cholecystokinin peptide is $^{111}$In-DTPA-[A-Asp$^{26}$,Nle$^{28,31}$]CCK.

Glucagon-like peptide-1 or GLP-1 is a peptide hormone that is synthesized in intestinal epithelial endocrine cells. GLP-1 is generated by alternative cleavage of proglucagon, and is found in two forms as GLP-1 (spanning amino acids 7-36) amide and GLP-1 (spanning amino acids 7-37).

Neuropeptide Y or NPY is a 36-amino acid neuropeptide that functions as a neurotransmitter in the brain and in the autonomic nervous system. The human neuropeptide Y is set forth in, e.g., Uniprot Accession No. P01303 or GenBank Accession No. NP_000896. The human neuropeptide Y mRNA (coding) sequence is set forth in, GenBank Accession No. NM_000905. NPY can include NPY analogs including Y1 and Y2 antagonists.

Octreotide or Sandostatin® is an octapeptide with a disulfide bridge. It can pharmacologically mimic somatostatin. The amino acid sequence of octreotide is set forth in SEQ ID NO: 7 (H-D-Phe-Cys-Phe-D-Trp-Lys-Thr-Cys-Thr-OH).

Edotreotide, DOTA$^0$-Phe$^1$-Tyr$^3$ or DOTA-TOC is a small molecule that can selectively bind to somatostatin receptors.

DOTA-TATE, DOTATATE or DOTA-octerotate is an amide of the acid DOTA and (Tyr$^3$)-octreotate. DOTA-TATE can selectively bind to somatostatin receptors.

Exendin-4 is a peptide hormone that can act as an agonist of the glucagon-like peptide (GLP) receptor. Exendin-4 can promote insulin secretion. Synthetic exendin-4 includes exenatide which is a 39-amino acid peptide. The amino acid sequence of exendin-4 is set forth in SEQ ID NO: 8 (HGEGTFTSDLSKQMEEEAVRLFIEWLKNGGPSS-GAPPPS-NH$_2$).

Soricidin is a 54-amino acid peptide. SOR-C13 and SOR-C27 are derived from the C-terminus of soricidin. They are high affinity antagonists of the calcium ion influx channels, TRPV channels. SOR-C13 and SOR-C27 can target tumors of the colon, prostate, and thyroid, as well as leukemias and lymphomas. The amino acid sequence of SOR-C13 is set forth in SEQ ID NO: 9(KEFLHPSK-VDLPR). The amino acid sequence of SOR-C27 is set forth in SEQ ID NO: 10 (EGKLSSNDTEGGLCKEFLHPSK-VDLPR). The amino acid sequence of soricidin is set forth in SEQ ID NO:11 (DCSQDCAACSILARPAELNTETCI-LECEGKLSSNDTEGGLCKEFLHPSKVDLPR).

3. Small Molecules

Non-limiting examples of small molecule VEGF receptor inhibitors include pazopanib (GW786034B; GlaxoSmithKline), GW654652 (GlaxoSmithKline), semaxanib (SU5416; Sugen), axitinib (INLYTA®, Pfizer), cabozantinib (COMTRIQ™, XL184; Exelixis), aflibercept (Sanofi-Aventis); brivanib (BMS-582664; Bristol-Myers Squibb), tivozanib (AV-651; AVEC, Pharmaceuticals), ramucirumab (CYRAMZA™; Eli Lilly and Company), motesanib (Takeda Pharmaceutical Company Limited), vatalanib (PTK787/ZK222584; Bayer Schering and Novartis), and cediranib (RECENTIN™, AZD 2171; AstraZeneca).

In some aspects, the IRDye® 700DX labeled probe is also conjugated to a radionuclide. Useful radionuclides include, but are not limited to, gamma-emitters, such as $^{111}$In, $^{99m}$Tc and $^{177}$Lu, beta-emitters, such as $^{90}$Y, $^{188}$Re, and $^{177}$Lu, and auger electrons of $^{111}$In.

In some aspects, the IRDye® 700DX labeled probe is further conjugated to a fluorophore. Suitable fluorophores include, but are not limited to, 4-acetamido-4'-isothiocyanatostilbene-2,2' disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Oregon Green; Cy 3; Cy 5; Cy 5.5; Cy 7; IRDye® 700; IRDye® 800CW; La Jolla Blue; phthalocyanine; naphthalocyanine ATT0647; and IRDye® 680LT.

C. Conjugating IRDye® 700DX to a Biomolecule Probe

The probe (e.g., peptide) can be conjugated to a phthalocyanine dye such as IRDye® 700DX (LI-COR, Lincoln, Nebr.). In some aspects, probes are labeled with IRDye® 700DX according to the manufacturer's protocols and kits. Detailed descriptions of methods for producing IRDye® 700DX-conjugates are found in, e.g., Kovar et al, Biochemistry—Faculty Publications, 2007, paper 9; Mitsunaga et al., Nature Medicine, 2011, 17:1685-1691; Peng et al., Proceedings of SPIE, 2006, 6097; U.S. Pat. Nos. 7,005,518 and 8,524,239; and U.S. Patent Application Publication No. 2013/0336995, the disclosures of each are herein incorporated in their entirety for all purposes.

Methods of linking dyes to various types of probes are well-known in the art. For a thorough review of, e.g., oligonucleotide labeling procedures, see R. Haugland in Excited States of Biopolymers, Steiner ed., Plenum Press (1983), Fluorogenic Probe Design and Synthesis: A Technical Guide, PE Applied Biosystems (1996), and G. T. Herman, Bioconjugate Techniques, Academic Press (1996).

IRDye® 700DX having a linker is shown below in Formula I:

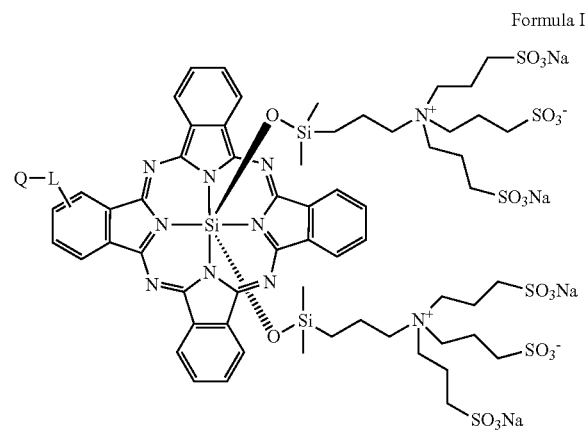

Formula I

In certain aspects, Q comprises a reactive group for attachment to a probe. Preferably, Q comprises a reactive group that is reactive with a carboxyl group, an amine, or a thiol group on the probe. Suitable reactive groups include, but are not limited to, an activated ester, an acyl halide, an alkyl halide, an optionally substituted amine, an anhydride, a carboxylic acid, a carbodiimide, a hydroxyl, iodoacetamide, an isocyanate, an isothiocyanate, a maleimide, an NHS ester, a phosphoramidite, a sulfonate ester, a thiol, or a thiocyanate (See Table 1 below).

L, in Formula I, is selected from a direct link, or a covalent linkage, wherein the covalent linkage is linear or branched, cyclic or heterocyclic, saturated or unsaturated, having 1 60 atoms selected from C, N, P, O, wherein L can have additional hydrogen atoms to fill valences (in addition to the 1-60 atoms), wherein the linkage contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds. In certain instances, L comprises a terminal amino, carboxylic acid, or sulfhydryl group and is represented as -L-NH$_2$, or -L-C(O)OH or -L-SH.

The linker "L-Q" can include a phosphoramidite group, an NHS ester, an activated carboxylic acid, a thiocyanate, an isothiocyanate, a maleimide and an iodoacetamide.

In certain aspects, the linker L comprises a —(CH$_2$)$_n$— group, wherein r is an integer from 1 to 10, preferably n is an integer from 1 to 5, such as 1 to 4, or 1, 2, 3, 4, or 5, and L-Q comprises a —O—(CH$_2$)$_n$—NH$_2$, or O—(CH$_2$)$_n$—C(O)OH or O—(CH$_2$)$_n$—SH.

In one aspect, L-Q in Formula I, is —O—(CH$_2$)$_3$—OC(O)—NH—(CH$_2$)$_5$—C(O)O—N-succinimidyl as shown below:

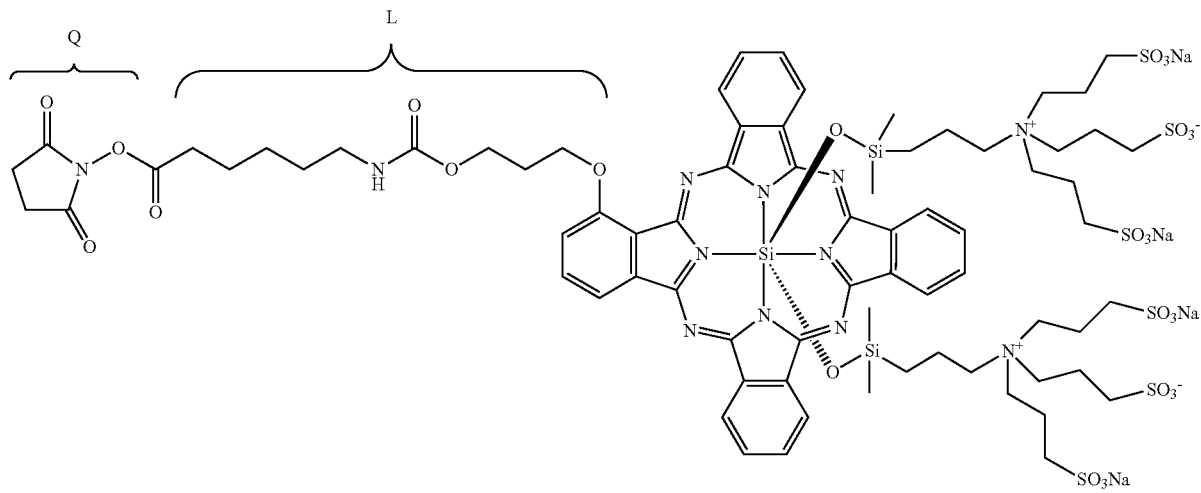

In certain instances, the dye is reacted with a probe having a primary amine to make a stable amide bond. In other aspects, a maleimide and a thiol can react together and make a thioether. Alkyl halides react with amines and thiols to make alkylamines and thioethers, respectively. Any derivative providing a reactive moiety that can be conjugated to a probe can be utilized herein. As is known in the art, moieties comprising a free amino group, a free carboxylic acid group, or a free sulfhydryl group provide useful reactive groups for protein conjugation. For example, a free amino group can be conjugated to proteins via glutaraldehyde cross-linking, or via carbodiimide cross-linking to available carboxy moieties on the protein. Also, a linker with a free sulfhydryl group can be conjugated to proteins via maleimide activation of the protein, e.g., using sulfosuccinimidyl-4-(N-maleimidomethyl)cyclohexane-1-carboxylate (Sulfo-SMCC), then linkage to the sulfhydryl group.

When linking a dye having a carboxylic acid group for attachment to an amine containing probe molecule, the carboxylic acid can first be converted to a more reactive form using an activating reagent, to form for example, a N-hydroxy succinimide (NHS) ester or a mixed anhydride. The amine-containing probe is treated with the resulting activated acid to form an amide linkage. One of skill in the art will recognize that alternatively, the NHS ester can be on the probe and the amine can be on the dye.

In other aspects, the linker is a member selected from the group of a PEG, a block copolymer of PEG-polyurethane and a PEG-polypropylene. In yet other aspects, the linker is a member selected from the group of a polysaccharide, a polypeptide, an oligosaccharide, a polymer, a co-polymer and an oligonucleotide.

The linker L can have the formula:

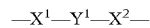

wherein: $X^1$ is a member selected from the group of a bivalent radical, a direct link, oxygen, an optionally substituted nitrogen and sulfur; $Y^1$ is a member selected from the group of a direct link and $C_1$-$C_{10}$ alkylene optionally interrupted by a heteroatom; and $X^2$ is a member selected from the group of a bivalent radical, a direct link, oxygen, an optionally substituted nitrogen and sulfur.

Preferably, the bivalent radical of $X^1$ and $X^2$ are each independently selected from the group of a direct link, optionally substituted alkylene, optionally substituted alkyleneoxycarbonyl, optionally substituted alkylenecarbamoyl, optionally substituted alkylenesulfonyl, optionally substituted alkylenesulfonylcarbamoyl, optionally substituted arylene, optionally substituted arylenesulfonyl, optionally substituted aryleneoxycarbonyl, optionally substituted arylenecarbamoyl, optionally substituted arylenesulfonylcarbamoyl, optionally substituted carboxyalkyl, optionally substituted carbamoyl, optionally substituted carbonyl, optionally substituted heteroarylene, optionally substituted heteroaryleneoxycarbonyl, optionally substituted heteroarylenecarbamoyl, optionally substituted heteroarylenesulfonylcarbamoyl, optionally substituted sulfonylcarbamoyl, optionally substituted thiocarbonyl, a optionally substituted sulfonyl, and optionally substituted sulfinyl.

Alternatively, the linker is —(CH$_2$)$_r$—, wherein r is an integer from 1 to 50.

The reactive Q group of Formula I reacts with a complementary group on the probe to form a compound of Formula Ia:

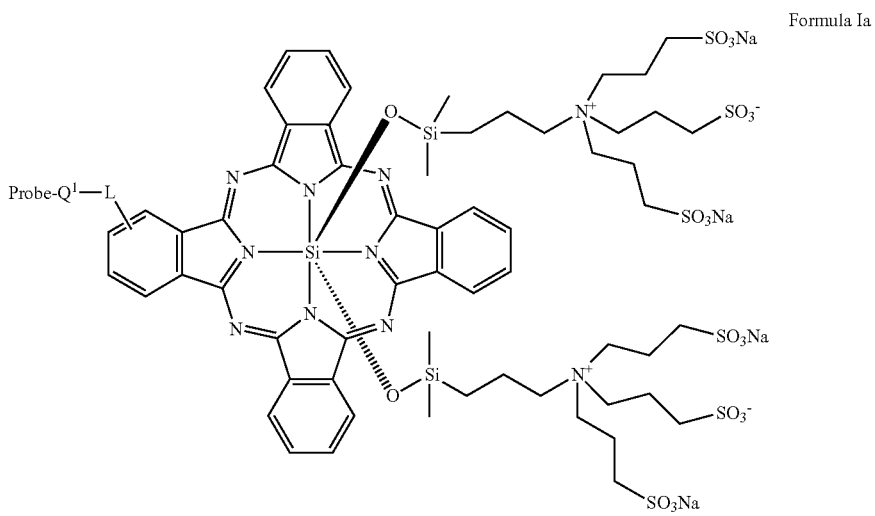

Formula Ia

In Formula Ia, the reactive Q group of Formula I reacts with a complementary group on the probe and forms a covalent linkage $Q^1$. The probe is then attached covalently to the linker.

In one aspect, IRDye® 700DX has an NHS ester as above and the probe has an amine, which reacts to form an amide:

IRDye® 700DX-O—$(CH_2)_3$—OC(O)—NH—$(CH_2)_5$—C(O)NH-Probe

Selected example of reactive functionalities useful for the attaching the dye to the probe are shown in Table I, wherein the bond results from the reaction of the dye (e.g., detecting agent or photosensitizing agent) with the probe. Those of skill in the art will know of other bonds suitable for use in the present invention.

TABLE 1

| A<br>Reactive functionality Q<br>on the phthalocyanine dye | B<br>Complementary group<br>on the probe | C<br>The resulting bond $Q^1$ |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| anhydrides | alcohols/phenols | esters |
| anhydrides | amines/anilines | carboxamides/imides |
| aryl halides | Thiols | thiophenols |
| aryl halides | amines | aryl amines |
| aziridines | thiols | thioethers |
| boronates | glycols | boronate esters |
| activated carboxylic acids | amines/anilines | carboxamides |
| activated carboxylic acids | alcohols | esters |
| activated carboxylic acids | hydrazines | hydrazides |
| carbodiimides | carboxylic acids | N-acylureas or anhydrides |
| diazoalkanes | carboxylic acids | esters |
| epoxides | thiols (amines) | thioethers (alkyl amines) |

TABLE 1-continued

| A<br>Reactive functionality Q<br>on the phthalocyanine dye | B<br>Complementary group<br>on the probe | C<br>The resulting bond $Q^1$ |
|---|---|---|
| epoxides | carboxylic acids | esters |
| haloacetamides | Thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonyl halides | amines/anilines | sulfonamides |

*Activated esters, as understood in the art, generally have the formula —COM, where M is a good leaving group (e.g. succinimidyloxy (—$OC_4H_4O_2$) sulfosuccinimidyloxy (—$OC_4H_3O_2SO_3H$), -1-oxybenzotriazolyl (—$OC_6H_4N_3$); 4-sulfo-2,3,5,6-tetrafluorophenyl; or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —$OCOR^a$ or $OCNR^aNHR^b$, where $R^a$ and $R^b$, which may be the same or different, are $C_1$-$C_6$ alkyl, $C_1$-$C_6$ perfluoroalkyl, or $C_1$-$C_6$ alkoxy; or cyclohexyl, 3-dimethylaminopropyl, or N-morpholinoethyl).
**Acyl azides can also rearrange to isocyanates.

In some aspects, the covalent linkage $Q^1$ between the linker and probe (Column "C") is selected from the group of a direct bond, an amide bond, an ester bond, an ether bond, an oxime bond, a phosphate ester bond, a sulfonamide bond, a thioether bond, a thiourea bond, and an urea bond. In an alternative embodiment, the "A" reactive functional group is on the probe and the complementary functional group "B" in on the dye.

In other aspects, IRDye® 700DX dye is linked to a probe or biomolecule by click chemistry. Click chemistry uses simple, robust reactions, such as the copper-catalyzed cycloaddition of azides and alkynes, to create intermolecular linkages. For a review of click chemistry, see, e.g., Kolb, H. C.; Finn, M. G.; Sharpless, K. B. *Angew. Chem.* 2001, 40, 2004.

Connection (or ligation) of two fragments to make a larger molecule or structure is often achieved with the help of so-called click chemistry described by Sharpless et al., *Angew. Chem.*, Int. Ed. 40: 2004 (2001). This term is used to describe a set of bimolecular reactions between two different reactants such as azides and acetylenes. The formation of 1,2,3-triazoles in 1,3-dipolar cycloaddition of azides to a triple bond is known, but because the activation energy of acetylene-azide cycloaddition is relatively high, the reaction is slow under ambient conditions.

The utility of the reaction of azides with alkynes was expanded by the discovery of Cu (I) catalysis. 1,3-cycloaddition of azides to terminal acetylenes in the presence of catalytic amounts of cuprous salts is *facile* at room temperature in organic or aqueous solutions.

U.S. Pat. No. 7,807,619 to Bertozzi et al. teaches modified cycloalkyne compounds and method of use of such compounds in modifying biomolecules. Bertozzi et al. teach a cycloaddition reaction that can be carried out under physiological conditions. As disclosed therein, a modified cycloalkyne is reacted with an azide moiety on a target biomolecule, generating a covalently modified biomolecule.

D. Therapeutic Uses of a IRDye® 700DX-Labeled Biomolecule Probe

In yet other aspects, the present invention provides methods and compounds for photodynamic therapy (PDT) of target cells, tissues, and organs in a subject. In some instances, the target cells are cells of a solid tumor. In other instances, the target cells are located in the vasculature of the subject. PDT is a two-step treatment process that may be used in a wide variety of cancers and diseased tissue and organs. The first step in this therapy is carried out by administering a photosensitizing agent systemically by ingestion or injection, or topically applying the compound to a specific treatment site on a subject, followed by the second step of illuminating the treatment site with light having a wavelength or waveband corresponding to a characteristic absorption waveband of the photosensitizing agent. The light activates the photosensitizing agent, causing singlet oxygen radicals and other reactive species to be generated, leading to a number of biological effects that destroy the abnormal or diseased tissue, which has absorbed the photosensitizing agent. The depth and volume of the cytotoxic effect (e.g., apoptotic effect) on the abnormal tissue, such as a cancerous tumor or leaking blood vessel, depends in part on the depth of the light penetration into the tissue, the photosensitizing agent concentration and its cellular distribution, and the availability of molecular oxygen, which will depend upon the vasculature system supplying the tumor, tissue, or organ.

In certain instances, the present invention provides methods for treatment, wherein for example, a tumor is treated using the therapeutic agent and thereafter, imaged to ascertain the extent of treatment. The treatment can be repeated until the tumor is destroyed or the site of treatment is satisfactorily complete. In certain instances, the methods include, injecting the probe or composition, treating the tumor using photodynamic therapy and thereafter imaging to ascertain the extent of treatment.

The method of the present invention provides for administering to the subject a therapeutically effective amount of a targeted photosensitizing agent, such as a therapeutic probe. The probe can be administered systemically by ingestion or injection, or locally administered to a target tissue site or to a surgical site. The agent can bind to one or more types of target cells or tissues, such as circulating tumor cells or cells of a solid tumor. When exposed to photoactivating light of an appropriate waveband, the agent absorbs the light, causing substances to be produced that impair or destroy the target cells or tissues via apoptosis. Preferably, the compound is nontoxic to the subject to which it is administered or is capable of being formulated in a nontoxic composition that can be administered to the subject. In addition, following exposure to light, the compound in any resulting photodegraded form is also preferably nontoxic.

The agent and activating light can be administered by any means known in the art for PDT, including, but not limited to, ingestion, injection, transcutaneous administration, transdermal administration, and transillumination. Preferably, the light is administered transcutaneously to a subject. For example, "transcutaneous" as used herein refers to the passage of light through unbroken tissue. Where the tissue layer is skin or dermis, transcutaneous includes "transdermal" and it will be understood that the light source is external to the outer skin layer. However, the term "transillumination" as used herein refers to the passage of light through a tissue layer, such as the outer surface layer of an organ, e.g., the liver, and it will be apparent that the light source is external to the organ, but internal or implanted within the subject or patient.

In some aspects, the forms of energy used for administering PDT include, but are not limited to, light (i.e., radiation), thermal, sonic, ultrasonic, chemical, light, microwave, ionizing (such as x-ray and gamma ray), mechanical, and electrical. The term "radiation" as used herein includes all wavelengths and wavebands. Preferably, the radiation wavelength or waveband is selected to correspond with or at least overlap the wavelengths or wavebands that excite the photosensitizing agent. Photosensitive agents typically have one or more absorption wavebands that excite them to produce the substances which damage or destroy target cells, tissues, organs, or tumors. Preferably, the radiation wavelength or waveband matches the excitation wavelength or waveband of the photosensitizing agent and has low absorption by the non-target cells and the rest of the subject, including blood proteins.

In further aspects, the target cell, tissue, organ, or tumor for treatment with PDT is selected from the group of vascular endothelial tissue, skin tissue, an abnormal vascular wall of a tumor, a solid tumor, a tumor of the head, a tumor of the neck, a tumor of a the gastrointestinal tract, a tumor of the liver, a tumor of the breast, a tumor of the prostate, a tumor of the ovary, a tumor of the uterus, a tumor of the testicle, a tumor of the lung, a nonsolid tumor, malignant cells of one of a hematopoietic tissue and a lymphoid tissue, lesions in the vascular system, a diseased bone marrow, and diseased cells in which the disease is one of an autoimmune and an inflammatory disease. In yet a further embodiment, the target tissue is a lesion in the vascular system of a type selected from the group of atherosclerotic lesions, arteriovenous malformations, aneurysms, and venous lesions.

IV. Examples

The following examples are offered to illustrate, but not to limit, the claimed invention.

Example 1. Stability of IRDye® 700DX Carboxylate at pH 2.1-8.2 and at Different Temperatures This example illustrates the stability of the IRDye® 700DX carboxylate in a range of pHs and temperatures. The carboxylate has the following structure:

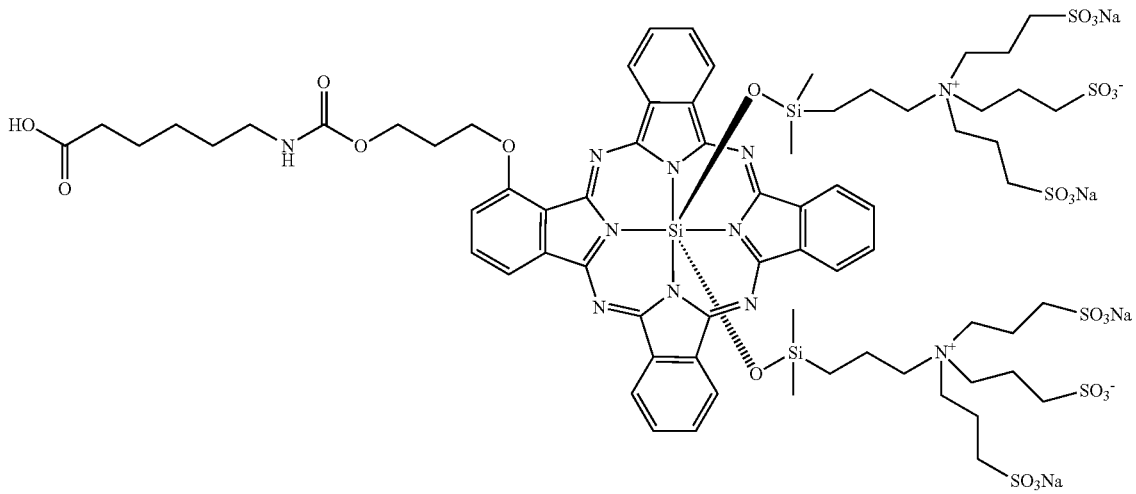

Figure 2:
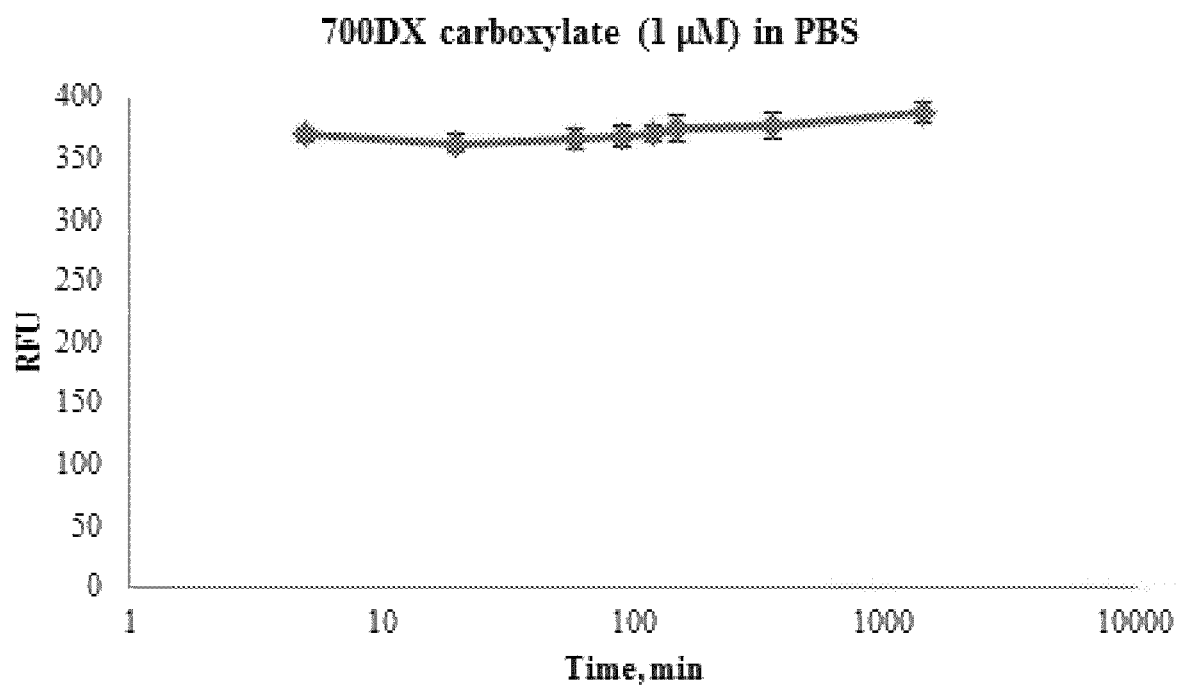
FIG. 2 illustrates the stability of IRDye® 700DX carboxylate in PBS at 37° C.
Figure 3A:
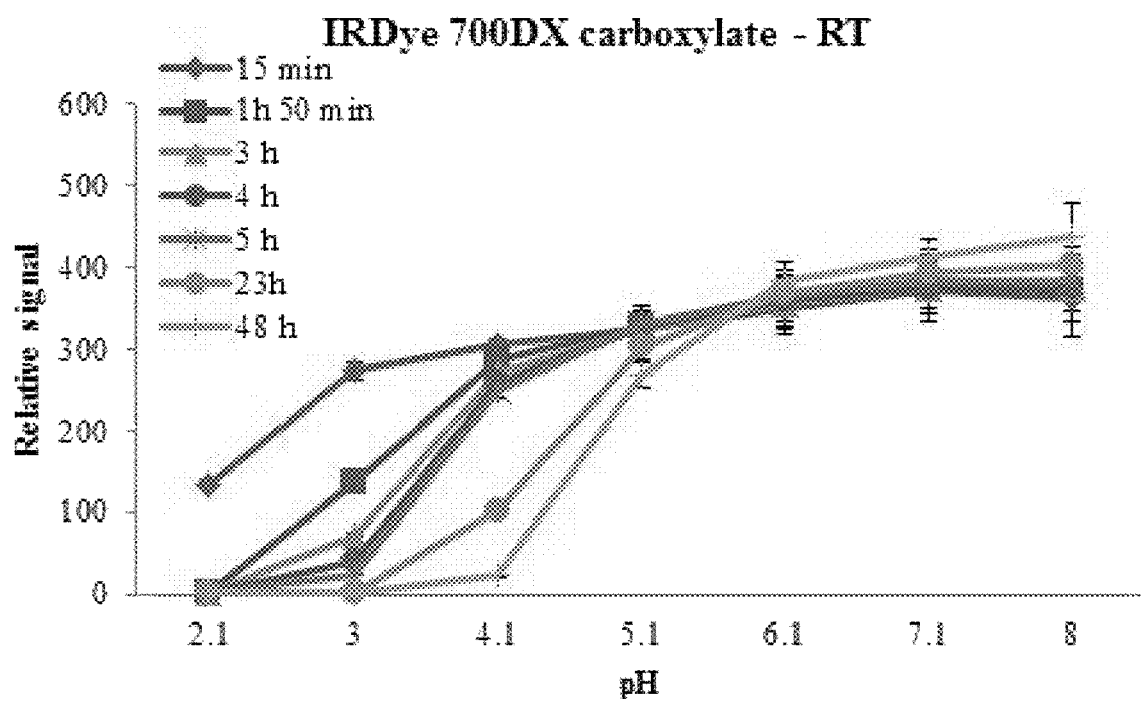
FIGS. 3A and 3B show the effect of pH on the signal intensity of IRDye® 700DX carboxylate.
Figure 3B:
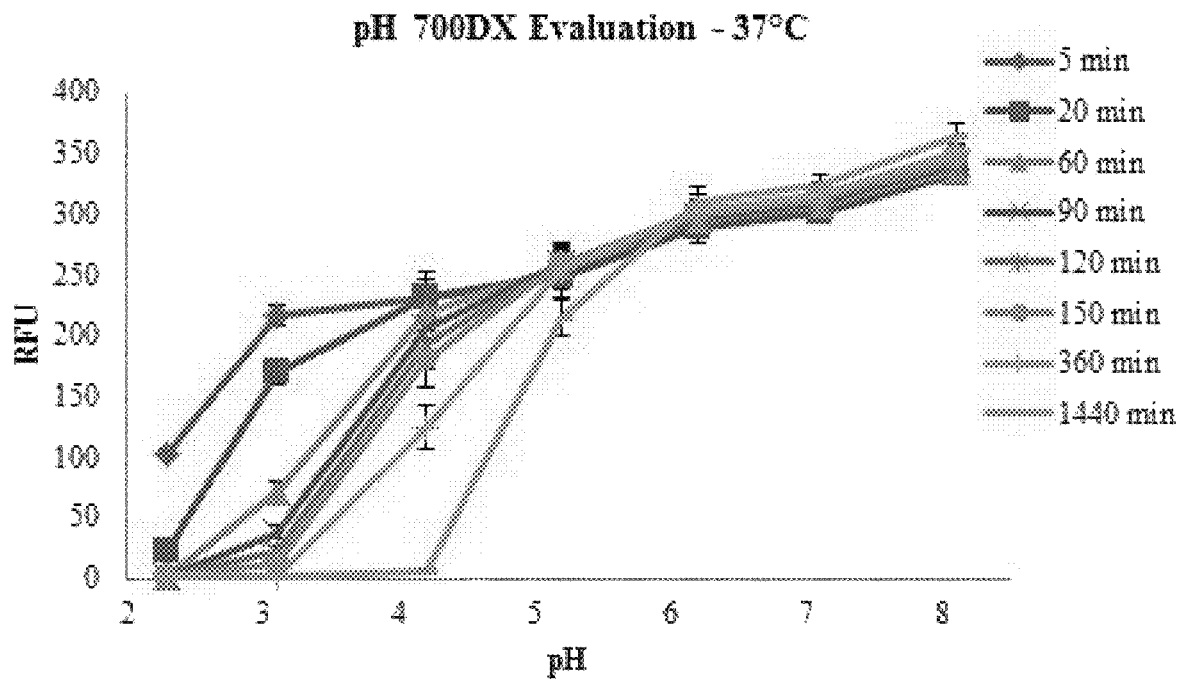

Evaluation of the effect of pH on the stability of the carboxylate form of the dye was performed at room temperature and at 37° C. For comparison purposes a test of the stability at 37° C. while dissolved in 1×PBS was included. Mcllaine's buffer solution with constant ionic strength was used. The test in PBS showed very little loss of signal intensity at 1 μM (FIG. 2). When the dye was dissolved in various buffers with increasing pH (2.1-8.2) a loss in signal intensity initially occurred between pH 4 and 5 with losses progressively increasing down to pH 2.1 at room temperature (FIG. 3A). At 37° C. this loss initially occurred at a slightly higher pH between pH 5-6 with a progression similar to the tests done at room temperature (FIG. 3B).

Example 2. Binding of IRDye® 700DX Carboxylate to Proteins

Many photosensitizers bind albumin or other serum proteins, thus allowing them to collect and localize preferentially in tumors. This example illustrates the binding of IRDye® 700DX to serum proteins as well as the binding of methylene blue to similar serum proteins.

In SDS-PAGE and under non-reducing conditions, ovalbumin has a molecular weight of about 40 kDa, 45 kDa, 63 kDa and 72 kDa. Human serum albumin (HSA) has a molecular with ranging from about 66.6 kDa to about 66.4 kDa or lower under non-reducing conditions. HSA can migrate as an approximately 58-67 kDa band in SDS-PAGE under reducing conditions.

Human serum albumin, bovine serum albumin, 5% FBS and IRDye® 700DX carboxylate were incubated in 1×PBS for 2.5 h at room temperature. Methylene blue was also used as a dye known to bind to albumin and the other serum proteins. The samples were run on a 4-12% Bis-Tris gel. Ovalbumin served as the negative control. The proteins incubated with IRDye® 700DX carboxylate are on the left of the gel and methylene blue samples are on the right (FIG. 4A-B).

Figure 4A:
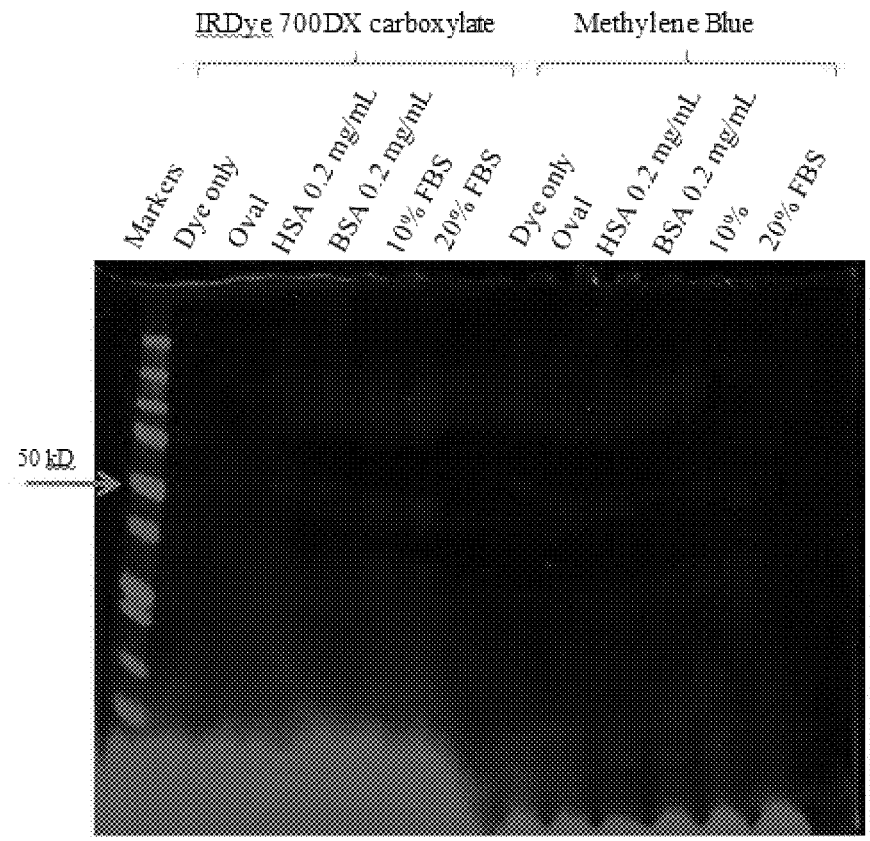
FIGS. 4A and 4B show the binding of IRDye® 700DX carboxylate to proteins, such as those found in human serum albumin (HSA), bovine serum albumin (BSA) and fetal bovine serum (FBS) after 1 hour incubation (FIG. 4A) and after a 2.5 hour incubation (FIG. 4B).
Figure 4B:
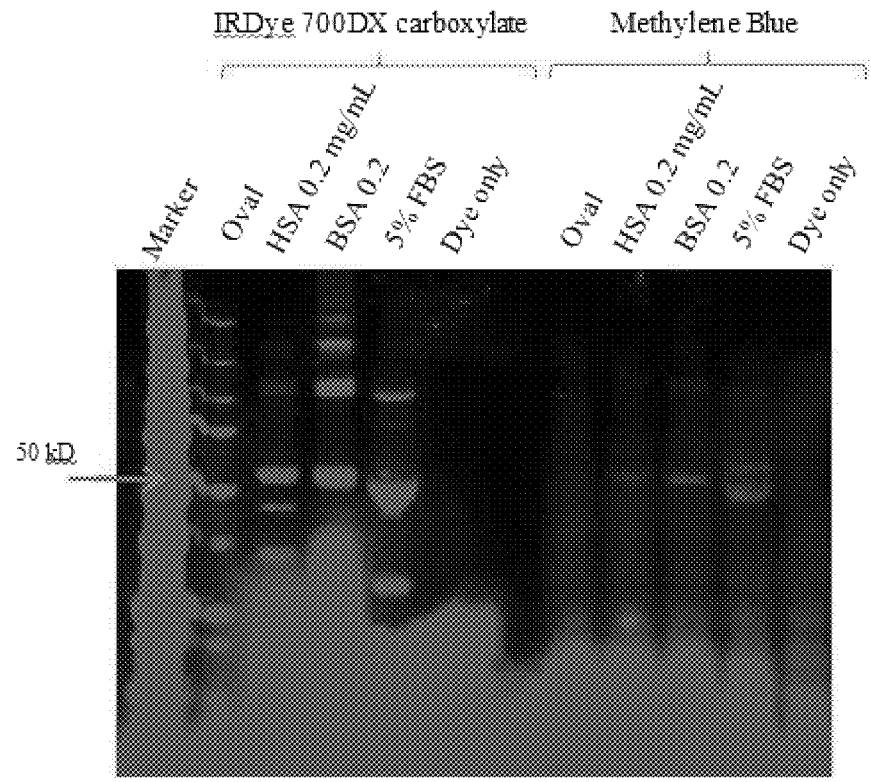

After 1 h post-incubation, measurable binding of IRDye® 700DX to the serum proteins including albumin is not detected (FIG. 4A). Free dye is visible at the bottom of the gel which indicates that dye is in excess and available for binding reactions. FIG. 4B shows after 2.5 h incubation, binding of 700DX to the serum proteins including albumin is evident. Signal is present for the methylene blue samples. Albumin is detected in the human serum albumin, BSA and FBS samples.

Example 3. Using IRDye® 700DX Conjugated Probes to Induce Cytotoxicity

This example illustrates the effect of photodynamic therapy based on IRDye® 700DX dye conjugates on cell morphology. Other methods for evaluating changes in morphology during the PDT with additional tests of key apoptotic markers including caspase 3/7, annexin-V, vitality %, mitochondrial potential, localization (intracellular/membrane, endosomal, lysosomal), singlet oxygen generation, other radicals, etc. It was critical to identify important parameters for generating reproducible effects including irradiation level, incubation time, probe type and/or required dose to initiate cytotoxicity. By measuring these key indicators the actions of IRDye® 700DX in its ability to induce cytotoxicity was defined.

Figure 5A:
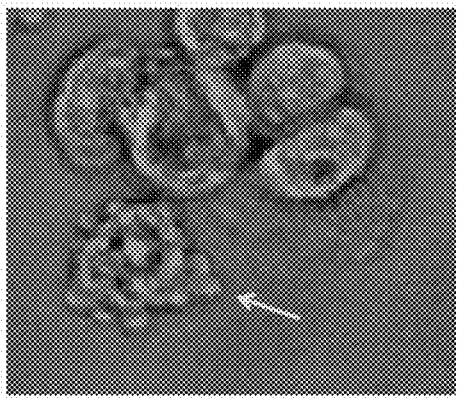
FIGS. 5A-C show blebbing of cell membranes (arrows) after irradiation (24 $J/cm^2$) in A431 cells incubated with IRDye® 700DX-EGF and irradiated.
Figure 5B:
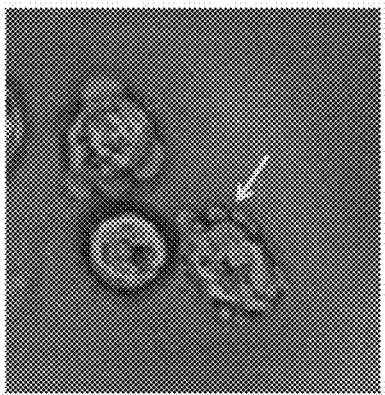
Figure 5C:
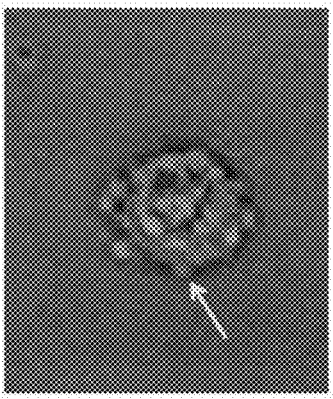

Morphology is a common indicator for defining cell changes after irradiation. FIGS. 5A-5C demonstrate the very early blebbing feature (highlighted by arrows) which is common to apoptosis and necrosis.

The experiments clearly demonstrated that IRDye® 700DX is the active component in PDT. FIGS. 6A-6B provide images of the controls which were A431 cells with no irradiation (NI) or with irradiation (I). The probe dose for the respective treatments was 0.25 μM and irradiation level was 16 J/cm². The results showed that cell morphology was unchanged for untreated cells, illustrating that the level of irradiation alone had no deleterious effect (FIG. 6B). An additional control included the incubation with IRDye® 700DX-EGF with NI (FIG. 6C), which also showed no deleterious effect on cell morphology demonstrating the requirement of irradiation in PDT. Lastly, when cells were treated with IRDye® 700DX-EGF and irradiated, their morphology was dramatically altered with condensation of nuclei and cell dehydration (FIG. 6D). These are key features of cells undergoing apoptosis and/or necrosis. When cell viability was measured 24 h post irradiation, the results confirmed that only the probe treated with irradiation induced cytotoxicity (FIGS. 6A-6D).

Example 4. Clearance Evaluation of IRDye® 700DX Carboxylate in Animal Models

This example illustrates the PDT effects of an IRDye® 700DX-antibody probe and an IRDye® 700DX-small protein ligand probe. The IRDye® 700DX-EGF probe was internalized after binding to its cognate receptor and was rapidly processed in minutes. The small molecule probe induced apoptosis, while the IRDye® 700DX-antibody probe induced necrosis.

It has been suggested that the mechanism of action with IRDye® 700DX for photoimmunotherapy (PIT) is different compared to PDT. To test this hypothesis two probes labeled with IRDye® 700DX-panitumumab (about 0.1 µM; antibody) and EGF (0.5 µM; small protein ligand) were evaluated. Both probes can bind EGFR and had approximately 2 dye molecule per conjugate molecule. It was assumed that the affinity for the receptor will be different for the antibody (generally pM), compared to the small protein (nM). Although the probe doses were different, the incubation times were the same at only 10 min. After incubation, the probes were rinsed from the cells. FIGS. 7A and 7B illustrates A431 cells that were incubated with IRDye 700DX-panitumumab or IRDye 700DX-EGF, respectively and thereafter irradiated. The probes showed similar effects on cell morphology as examined 24 hours post irradiation. The level of cytotoxicity was different for the two probes, indicating that the two probes initiate cytotoxicity through two different pathways, such as the apoptosis and necrosis pathways. 62% of the irradiated cells treated with IRDye® 700DX-panitumumab were dead and 36% of the irradiated cells treated with IRDye® 700DX-EGF were dead.

IRDye® 700DX-panitumumab probe was located on the cell surface and associated with the membrane. Thus, upon irradiation, the production of singlet oxygen occurred at the cell surface. Typically, the EGF ligand is internalized after binding the EGF receptor. As such, the IRDye® 700DX-EGF probe was endocytosed by the cell and generated cytotoxic reactive oxygen species within the cell.

Figure 8A:
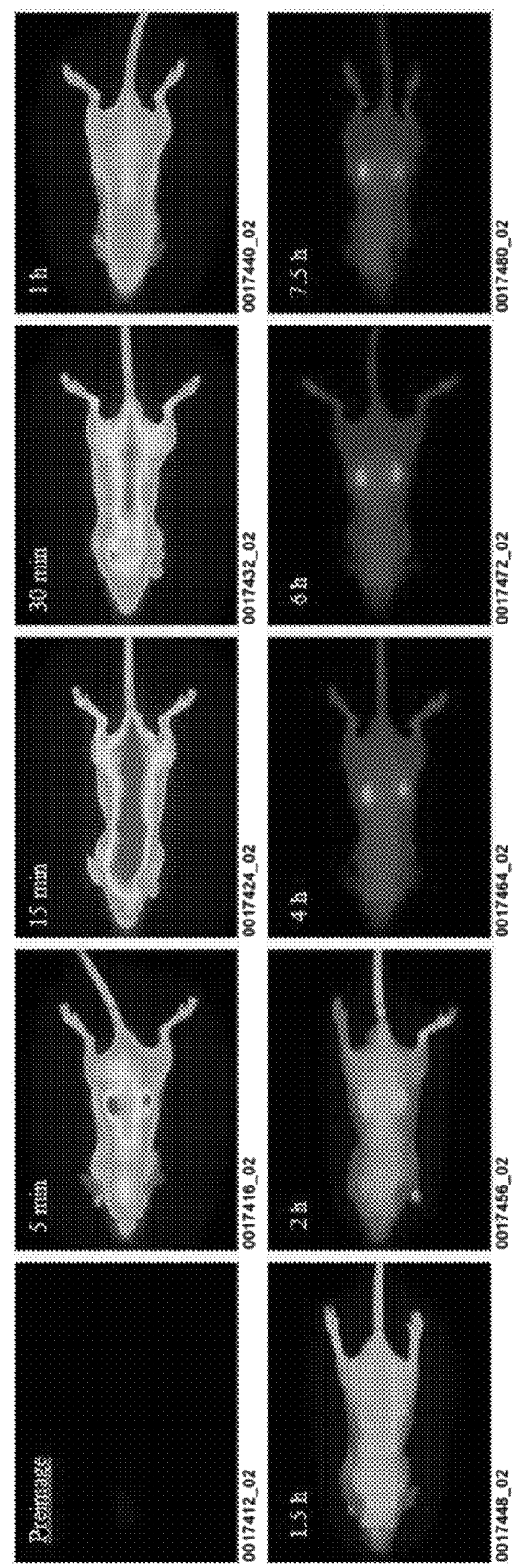
FIGS. 8A-8B show the clearance and biodistribution of IRDye® 700DX in vivo.
Figure 8B:
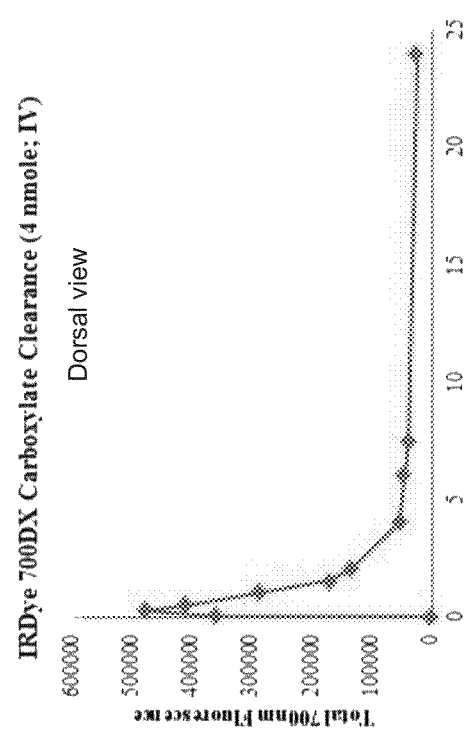
Figures 9A, 9B:
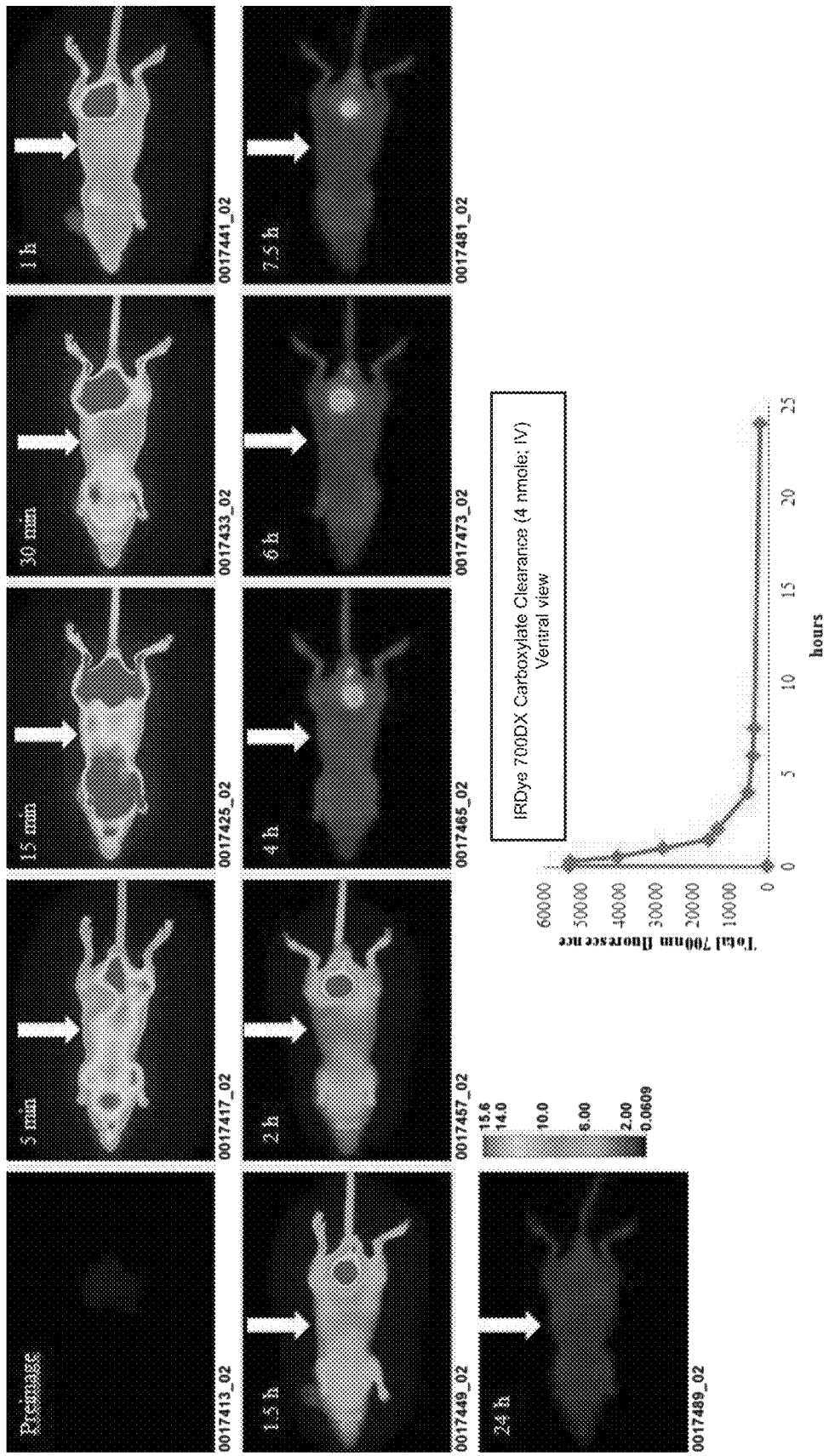
FIGS. 9A-9B show the clearance and biodistribution of IRDye® 700DX in vivo.
Figure 10A:
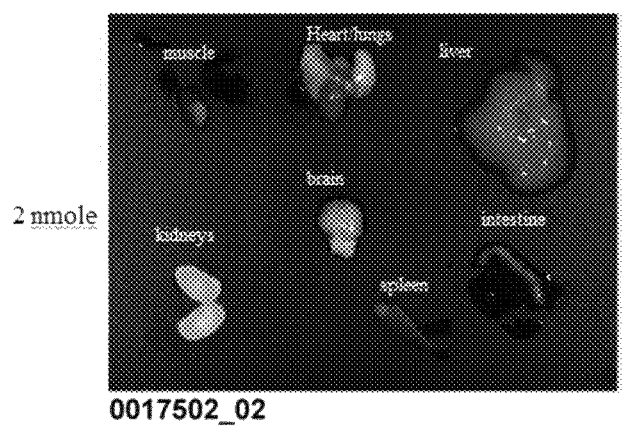
FIGS. 10A-10C illustrate the presence of the dye in organs harvested from a nude mouse administered IRDye® 700DX.
Figure 10B:
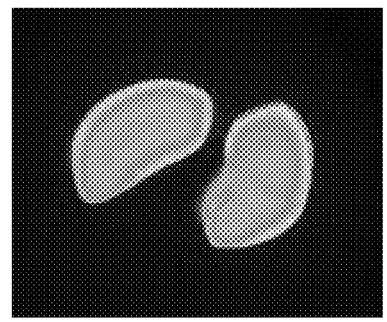
Figure 10C:
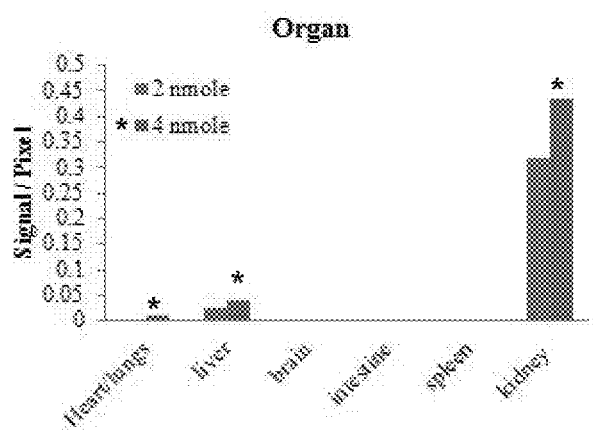

Experiments were performed to evaluate the clearance of IRDye® 700DX carboxylate in nude mice receiving 2 or 4 nmoles of the compound. This is the non-reactive form of the dye and the in vivo elimination kinetics can be used to determine the biodistribution of the dye and a subsequent dye-labeled conjugate. The results for both doses were very similar (only 4 nmole animal images are presented). Clearance appeared to be renal as noted in the dorsal (FIG. 8A) and ventral whole body views (FIG. 9A). The kidneys are visible throughout the dorsal series (FIG. 8A) and liver negligible in ventral series (FIG. 9A). The kidney signal exceeds liver suggesting no significant retention in the liver and renal excretion is primary route of elimination (FIG. 10A-10C). A closer examination of the organs after excision is illustrated in FIG. 10B (2 nmole dose). A longitudinal slice through the kidney (4 nmole dose) showed the primary location of the dye was in the proximal tubules of the renal cortex. This was seen in all animals regardless of the dye concentration. All organs imaged (muscle, heart, lungs, liver, brain, spleen, intestine, and kidneys) were analyzed for signal corrected for area. Graphical representation is presented in FIG. 10C. Interestingly, dose did not affect the amount of dye retained in the kidney dramatically. This may suggest that the dye is continually and very rapidly cleared by the body.

Example 5. Evaluation of the Therapeutic Effect of IRDye® 700DX-Labeled Antibody, Panitumumab Although the assumption is that the doses used in the assay described herein are too low to be a contributing factor in the cell death seen with IRDye® 700DX-labeled panitumumab, a small study was conducted to confirm that no therapeutic effect is due to the assay system. The test included the following four treatments: treatment 1 of unlabeled panitumumab and no irradiation (FIG. 11A), treatment 2 of IRDye® 700DX-labeled panitumumab and no irradiation (FIG. 11B), treatment 3 of unlabeled panitumumab and irradiation (FIG. 11C), and treatment 4 of IRDye® 700DX-labeled panitumumab and irradiation (FIG. 11D). The irradiation dose was 24 J/cm$^2$ with the probe incubation of 10 minutes and a concentration of 0.1 µM. FIG. 11E shows the percentage of necrotic cells post-treatment and after incubation for 24 hours at 37° C. The morphology data showed that only treatment 4 of the labeled panitumumab and irradiation (FIG. 11D) effectively induced cell death. No measurable effect was observed for unlabeled or labeled-antibody without irradiation (FIG. 11A-11C). The data indicates that the antibody is not providing any significant effect in the assay system used.

A different LED source was tested and evaluated to determine if a second source of LED would yield a similar effect as the standard LED used. A straight forward evaluation was set up with four treatments (treatments A-D). The tests were performed in triplicate in order to examine reproducibility. The test included the following four treatments: treatment A of no probe and irradiation, treatment B of IRdye® 700DX-labeled EGF and no irradiation, treatment C of IRDye® 700DX-labeled EGF and irradiation, and treatment D of IRDye® 700DX-labeled panitumumab and irradiation. The probe dose was about 0.1 µM labeled panitumumab and 0.5 µM 700DX-labeled EGF. Irradiation was for 10 minutes at an irradiation dose of 32 J/cm$^2$.

FIGS. 12A-12D shows the morphology of cells from a representative treatment for each respective probe with the corresponding 700 nm image to illustrate how effective labeling was prior to irradiation.

Figure 12A:
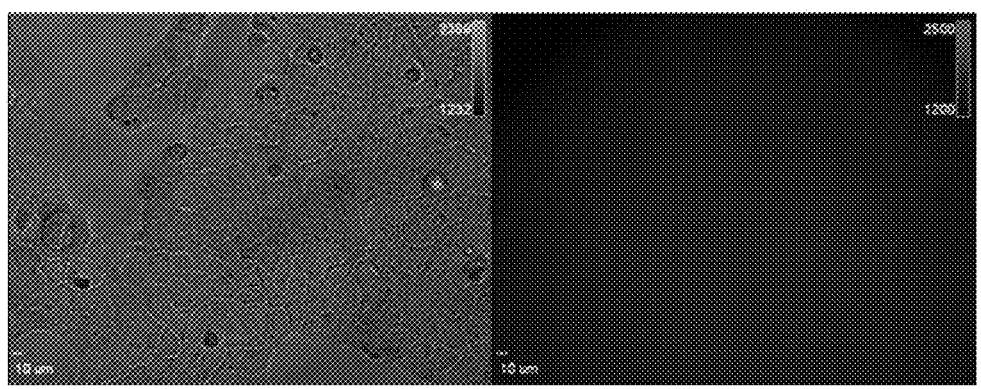
FIGS. 12A-D show the effect of the IRDye® 700DX-EGF with and without irradiation compared to the positive control, IRDye 700DX-panitumumab on necrosis and cell morphology.
Figure 12B:
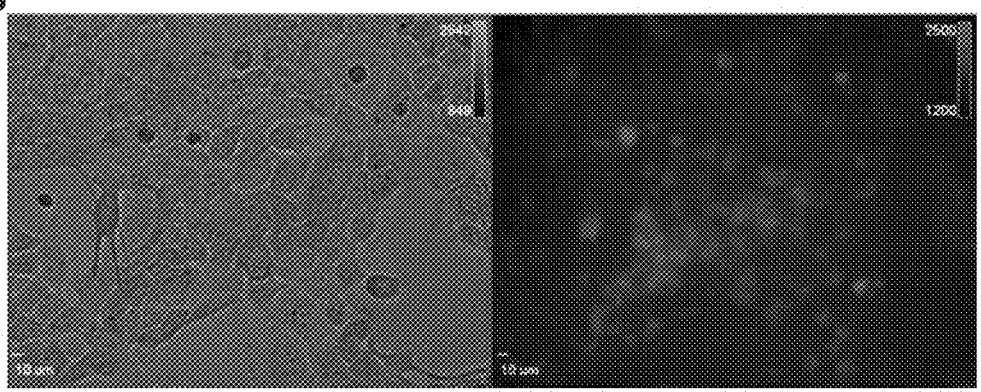
Figure 12C:
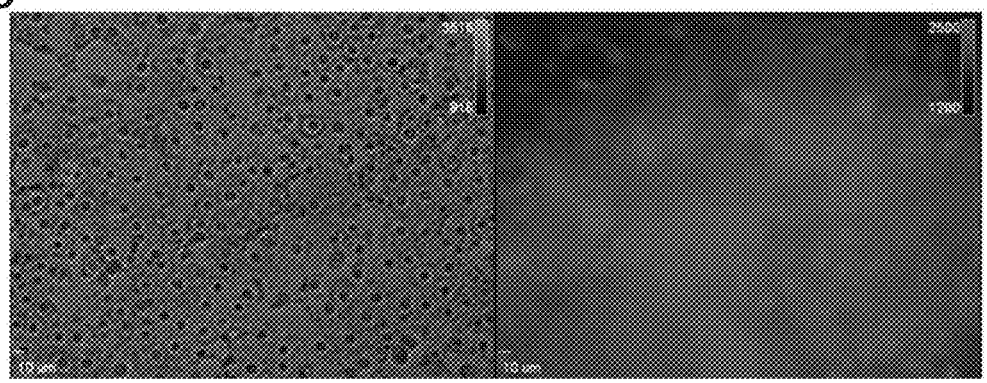
Figure 12D:
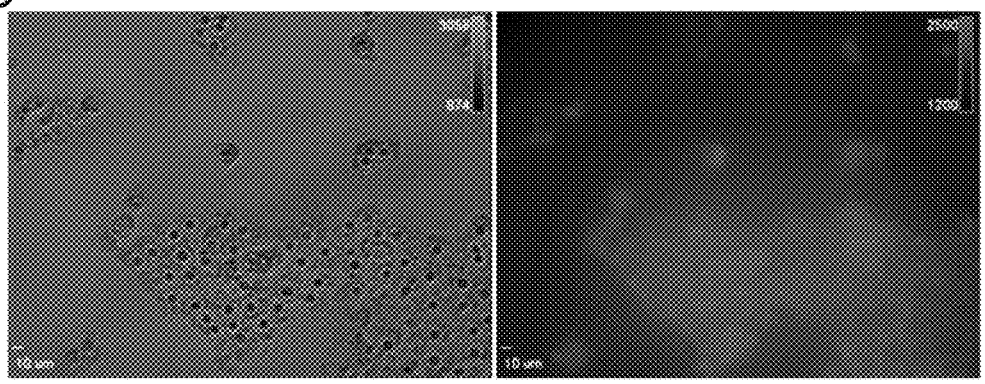
Figure 14A:
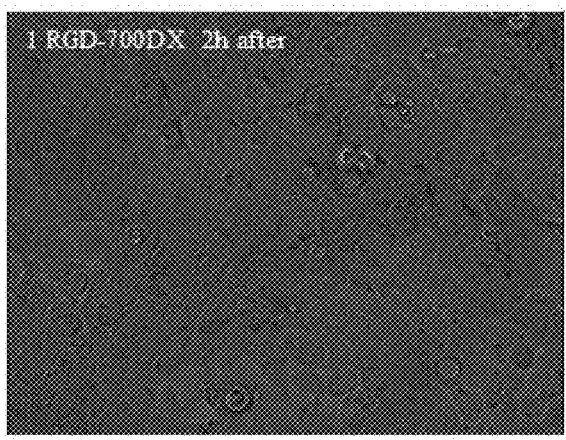
FIGS. 14A-14D shows DIC images of cells that received treatments 1 (FIG. 14A), 3 (FIG. 14B), 5 (FIG. 14C) or 7 (FIG. 14D) 2 hours post-irradiation.
Figure 14B:
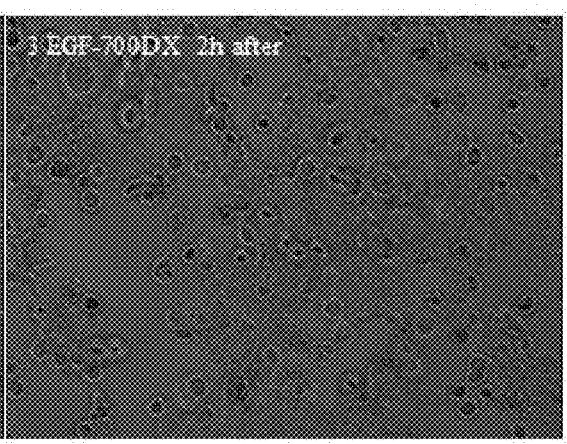
Figure 14C:
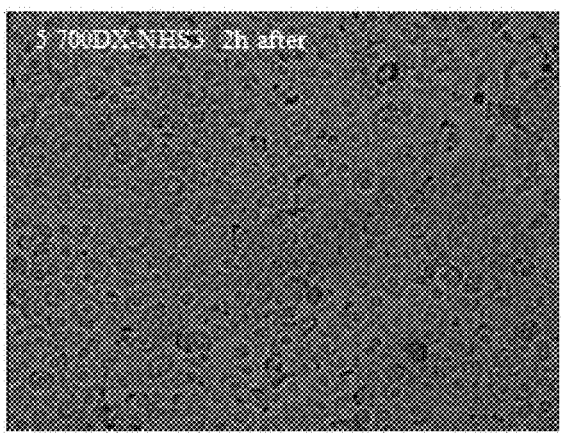
Figure 14D:
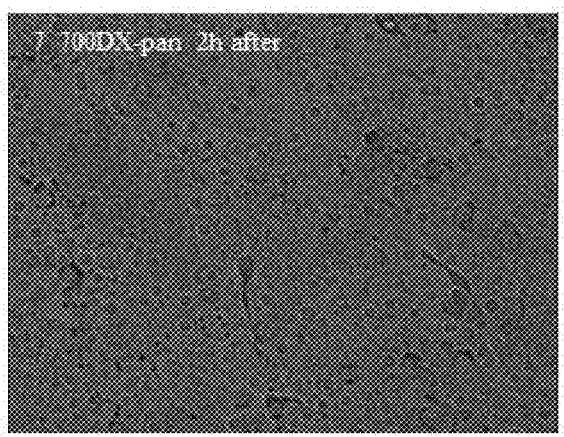

Analysis of cell treated with either IRDye® 700DX-EGF or IRDye® 700DX-panitumumab were severely affected by the irradiating energy and were dying (FIGS. 12C and 12D, respectively). Significant and similar effects for both probes together and in triplicate thus providing clear evidence that IRDye® 700DX-labeled small protein can kill cells similarly to an IRDye 700DX-labeled antibody. The % necrosis and % viability is provided in Table 2 below. Conditions for use of either probe may be unique to the individual probe. The data also shows that irradiation of cells alone failed to cause any effect, thereby suggesting that the dose of irradiation is not causing undue harm to the cells. The fluorescent scale of the 700 nm images was the same for both treated sets of cells (FIGS. 12C-12D). Although the exact concentration of the antibody probe is not known, the signals from the different probes appear similar in level and intensity.

TABLE 2

The effect of IRDye ® 700DX-labeled EGF and IRDye ® 700DX-labeled antibody on cell vitality, necrosis and viability

| | Treatment | % Vitality | Cells/mL | VB-48 % necrotic | % Viability, VB-48 assay |
|---|---|---|---|---|---|
| 1 | No probe I | 97.3 | 1.2 × 10$^6$ | 14 | 80-90 |
| 2 | No probe I | 97.4 | 9.3 × 10$^5$ | 11 | 80-90 |
| 3 | No probe I | 97.3 | 8.1 × 10$^5$ | 11 | 80-90 |
| 4 | 700DX-EGF NI | 97.9 | 6.6 × 10$^5$ | 11 | 80-90 |
| 5 | 700DX-EGF NI | 98.3 | 8.0 × 10$^5$ | 12 | 80-90 |
| 6 | 700DX-EGF NI | 96.0 | 7.7 × 10$^5$ | 10 | 90-100 |
| 7 | 700DX-EGF I | 33.0 | 2.8 × 10$^5$ | 70 | 40-50 |
| 8 | 700DX-EGF I | 50.8 | 4.1 × 10$^5$ | 55 | 40-50 |
| 9 | 700DX-EGF I | 84.6 | 3.8 × 10$^5$ | 31 | 60-70 |
| 10 | 700DX-Pan I | 14.6 | 2.8 × 10$^5$ | 67 | very low |
| 11 | 700DX-Pan I | 21.1 | 4.2 × 10$^5$ | 87 | very low |
| 12 | 700DX-Pan I | 10.4 | 2.3 × 10$^5$ | 87 | very low |

Example 6. Therapeutic Effect of Administering IRDye® 700DX-Labeled Small Molecules and NHS Ester This example shows an evaluation of various targeting agents and IRDye 700DX NHS ester labeling of cells. A small molecule RGD labeled probe was tested. It should be noted that A431 cells express very low levels of integrin receptors and are not the ideal cell type for this probe.

Briefly, A431 cells were labeled with respective probes for specific treatments (listed below); cells were rinsed and evaluated for labeling. The test include the following treatments: treatments 1-2 of RGD-IRDye® 700DX at 1 µM and radiation, treatments 3-4 of EGF-IRDye® 700DX at 0.5 µM and radiation, treatments 5-6 of IRDye® 700DX NHSe at 5 µM and radiation, treatments 7-8 of panitumumab-IRDye® 700DX at about 0.1 µM and radiation, treatment 9 of a negative control with no probe and no irradiation, and treatment 10 of RGD-IRDye® 700DX and no irradiation. The probes were incubated for about 10 minutes and with a longer period of about 20 minutes for the RGD probe. The cells were monitored with microscopy and morphology was examination 24 hours post treatment.

FIGS. 13A-13G shows the morphology of cells that received treatments 1, 3, 5 or 7 with the corresponding 700 nm image to illustrate how effective labeling was prior to irradiation. Low binding was expected for the RGD probe due to the low level of integrin receptors on A431 cells. Treatments 3, 5 and 7 all showed cytotoxicity with the most effective being the NHSe and panitumumab probes. FIGS. 14A-14D shows DIC images of cells that received treatments 1 (FIG. 14A), 3 (FIG. 14B), 5 (FIG. 14C) or 7 (FIG. 14D) at 2 hours post-irradiation. By 3 hours post-irradiation all treatments except RGD (Treatment 1) show significant cytotoxicity. Vitality, viability and necrosis assays such as a VB-48 assay and JC-1 assay were performed. The data is provided in Table 3.

TABLE 3

% vitality, viability and necrosis of treatments 1-10.

| VB-48 Assay | Treatment | (32 J/cm$^2$) Irradiation | Cells/mL | Est % Viability | % Healthy | Low % Vitality | % Necrotic |
|---|---|---|---|---|---|---|---|
| 1-2 | RGD-700DX (0.5 µM) | I | 6.6 × 10$^5$ | 90-100 | 91.6 | 2 | 7 |
| 3-4 | EGF-700DX (0.5 µM) | I | 3.4 × 10$^5$ | 60-70 | 60 | 19 | 20 |
| 5-6 | 700DX NHSe (5 µM) | I | 1.8 × 10$^5$ | 20-30 | 2.5 | 25 | 72 |
| 7-8 | Pan-700DX (~0.1 µM) | I | 1.2 × 10$^5$ | 30-40 | 15.0 | 15 | 70 |
| 9 | Control | NI | 6.4 × 10$^5$ | 90-100 | 94.8 | 3 | 2 |
| 10 | RGD-700DX (0.5 µM) | NI | 5.8 × 10$^5$ | 90-100 | 90.8 | 4 | 5 |

Example 7. Effect of Administering Various Doses of IRDye® 700DX-Labeled EGF to Induce Cell Death This example shows that treatment with a labeled EGF probe and irradiation can induce cell death. A431 cells were treated with IRDye® 700DX-labeled EGF at a concentration of about 0.1-1 µM for about 8 minutes and irradiated at about 32 J/cm$^2$.

Briefly, 150,000 cells were plated and incubated overnight at 37° C., 5% CO$_2$. About 1 ml of the probe was added to the appropriate treatments. The cells were rinsed after the incubation period and imaged. The cells were irradiated with a small LED apparatus. The cells were further incubated at 37° C., 5% CO$_2$, and then imaged at 2-3 hours post irradiation. The cells were then harvested and resuspended in 250 µl PBS. The cells were counted in NC-100™ NucleoCounter® (ChemoMetec A/S; Allerod, Denmark). The cells were analyzed according to manufacturer's protocol to perform the caspase3/7 assay (ImmunoChemistry Technologies, LCC, Bloomington, Minn.). The data is provided in Table 4. NC indicates negative control, e.g., no probe.

TABLE 4

% of apoptotic and necrotic cells following treatments 1-6.

| Treatment | Irradiation | Cells/mL | % Healthy | Early % Apoptotic | Late % Apoptotic | % Necrotic |
|---|---|---|---|---|---|---|
| NC | No Irradiation | 4 × 10$^5$ | 84 | 7 | 4 | 5 |
| EGF-700DX (1 µM) | Irradiation | 4 × 10$^5$ | 52 | 9 | 24 | 15 |
| EGF-700DX (1 µM) | No Irradiation | 5.4 × 10$^5$ | 87 | 6 | 4 | 3 |
| EGF-700DX (0.5 µM) | Irradiation | 4 × 10$^5$ | 52 | 6 | 26 | 17 |
| EGF-700DX (0.25 µM) | Irradiation | 4.8 × 10$^5$ | 61 | 5 | 18 | 16 |
| EGF-700DX (0.1 µM) | Irradiation | 4.6 × 10$^5$ | 72 | 8 | 11 | 10 |

Measurements of caspase 3/7 activity for the treatments show an effect of probe dose when using IRDye® 700DX EGF. When treatment 1 and 3 (receiving no irradiation) were tested they showed highest % healthy cells and lowest caspase activity (FIGS. 15A and 15C). An effect of concentration was detected as the percent of healthy cells dropped with increasing probe doses (FIGS. 15B, 15D-15G). The percent of late apoptosis increased with increasing doses. Little difference was noted between the two highest doses (1 µM and 0.5 µM) tested. The upper maximum of the dosing may have been reached in this system because no further effect was seen. In summary, cells treated with IRDye® 700DX-labeled EGF ligand undergo apoptosis when exposed to irradiating light at about 32 J/cm$^2$.

Example 8. Producing IRDye® 700DX Conjugated Chlorotoxin (CLTX-700DX)

Chlorotoxin (AnaSpec, AS-60770) is reconstituted at 1 mg/mL in PBS buffer pH 8.5. IRDye 700DX NHSE (LI-COR, P/N 929-70010) is reconstituted in PBS buffer pH 8.5 to 1 mg/mL. The dye is immediately added at a 2-3 molar equivalent to the chlorotoxin and allowed to incubate for 2 hours at room temperature in the dark. The IRDye 700DX-chlorotoxin is purified utilizing a Slide-A-Lyzer dialysis cassette (Pierce) to remove the unconjugated free dye.

Example 9. Characterizing IRDye® 700Dx Small Molecule Conjugates—IRDye® 700DX-Labeled CLTX (Chlorotoxin) and IRDye® 700DX-Labeled Anti-EGFR Affibody®

This example illustrates the use of IRDye® 700Dx small molecule conjugates (probes) to induce programmed cell death, i.e., apoptosis in cells. The small molecule conjugates described herein include IRDye® 700DX CLTX (chlorotoxin) and IRDye® 700DX anti-EGFR Affibody®.

Chlorotoxin (CLTX) is a 36 amino acid peptide found in venom of Leiurus quinquestriatu. It can block small-conductance chlorine channels. The molecule has also been shown to bind annexin A2 receptors and has a dual effect on the enzymatic activity of MMP-2.

Affibody® (Affibody, Solna Sweden) affinity ligands are described as antibody mimetics with superior characteristics. They are approximately 6 kDa in size and no Fc function. Affibodies also incorporate the Albumod™ technology that extends their circulatory half-life through a strong binding to albumin. Commercially available Affibody® molecules include anti-EGFR Affibody®, anti-ErbB2 Affibody®, anti-fibrinogen Affibody®, anti-insulin Affiboy®, anti-TNFα Affibody®, anti-transferrin Affibody®, etc.

A. IRDye 700DX-Labeled CLTX

The procedure of labeling CLTX with IRDye® 700Dx is similar to that of labeling CLTX with IRDye® 800 CW (Kovar et al., *Anal i*, 2013, 440(2):212-9). The basic structure was not altered and binding occurs with exposed lysine residues. The D/P ratio was ~2. Dilutions were made and run on a bis-Tris glycine gel for visualization. The overall size of the labeled molecule was estimated to be about 5950 MW.

For the treatment study, HTB-186 cells (a desmoplastic cerebellar medulloblastoma cell line) were prepared and plated in petri dishes. The cells were incubated overnight at 37° C., 5% $CO_2$. Treatments with respective probe and irradiation levels are presented in Table 5. The treatment dose was 10 µl per 500 µl plate. The probes were incubated on the cells for about 5 hours at 37° C., 5% $CO_2$.

TABLE 5

Treatment Conditions.

| # | Probe | Irradiation |
|---|---|---|
| 1 | Control: No probe | No IRR |
| 2 | Control: No probe | 32 J/cm$^2$ |
| 3 | CLTX-700DX (0.2 µg/ml) | No IRR |
| 4 | CLTX-700DX (0.2 µg/ml) | 16 J/cm$^2$ |
| 5 | CLTX-700DX (0.2 µg/ml) | 32 J/cm$^2$ |

At several timepoints post irradiation, cells were evaluated for morphology changes using epi-fluorescent microscope. Treatments were imaged after incubation with probe and before irradiation to document morphology. In addition, cells were images at the following timepoints: immediately after, 1 h, 2 h, and 24 h post irradiation.

Immediately after incubation and prior to irradiation, the cells from all the treatments (treatments 1-5) were healthy in appearance. No change in cell morphology was detected in any of the treatments. Those treatments receiving probe (treatments 3-5) showed similar punctate incorporation of the probe into the cell. 700 nm images showed the probe was internalized into the cells by endocytosis.

Immediately after irradiation, the cell morphology still remained healthy for all treatments including those receiving irradiation (treatment 2, 4 and 5). Signals captured in the 700 nm channel show that the probe intensity was similar among cells receiving probe (treatments 3, 4, and 5).

At 2 h post irradiation the punctate pattern of the probe remained unchanged from the initial images for the treatment receiving no irradiation (treatment 3). However, a change was detected for treatment 5 which received the highest level of irradiation. The punctate pattern appeared brighter and more intracellularly located. The morphology of the cells of treatment 5 remained normal compared to the other treatments.

At 24 hours post irradiation, the discernible changes in the 700 nm signal noted at 2 h appears were more pronounced. The bright signals from the probe were now localized inside the cells and in some cases, in particular regions of the cells. In addition, the characteristic blebbing and rounded appearance indicative of cells undergoing apoptosis was also detected.

The appearance of blebbing of the cells after more than 2 hours post irradiation suggests that the cells are undergoing apoptosis, and not necrosis which occurs on a faster time frame. For example, a necrotic response to an photodynamic antibody probe occurs within 15 minutes post irradiation.

To further investigate the subcellular localization of the IRDye® 700Dx small molecule probe, we used fluorescent organelle specific dyes to look for colocalization. We used MitoTracker® Green specific to the mitochondria to determine if the internalization of CLTX-700DX placed the probe at the mitochondrial. HTB-186 cells were plated on glass coverslips in petri-dishes and allowed to equilibrate for 24 h in complete media. The cells were incubated with CLTX-700DX for 4-5 h after which the cells were irradiated at 32 J/cm$^2$. Plates were incubated for an additional 24 h at 37° C. 5% $CO^2$. Cells were treated for 45 min with MitoTracker® Green per manufacturer's instruction. Cells were gently rinsed and incubated for 15 min with DAPI to stain the nuclei. Additional rinses were performed and the coverslip mounted on glass slides with Fluoromount™ medium. Microscopy imaging was performed to document location of the fluorophores and probe.

Microscopy analysis reveals that the CLTX-700DX probe was not located in the mitochondria or nuclei. The punctate pattern of the probe visualized 4-5 hours after incubation shows that the probe is internalized by the cell by endocytosis.

B. IRDye® 700DX-Labeled Anti-EGFR Affibody®

The anti-EGFR Affibody® was conjugated with IRDye® 700DX via the specific cysteine residue engineered on the Affibody®. IRDye® 700DX maleimide was prepared and effectively used to label at a D/P of 1.

For the treatment study, A431 cells (an epidermoid carcinoma cell line) were seeded on a coverslip in a petri-dish and incubated for 24 h. The cells were incubated overnight at 37° C., 5% $CO_2$. Treatments with respective probes and irradiation levels are presented in Table 6. The treatment dose was 10 µl per 500 µl plate. The probes were incubated on the cells for about 4-5 hours at 37° C., 5% $CO_2$. Cells were rinsed and irradiated at levels shown above. Petri-dishes were placed back in the incubator for up to 24 h.

TABLE 6

Treatment conditions.

| # | Probe | Irradiation |
|---|---|---|
| 1 | Control: No probe | No IRR |
| 2 | Control: No probe | 32 J/cm$^2$ |
| 3 | 700DX-EGFR Affibody ® | No IRR |
| 4 | 700DX-EGFR Affibody ® | 16 J/cm$^2$ |
| 5 | 700DX-EGFR Affibody ® | 32 J/cm$^2$ |

Images were captured before irradiation and then at 1 h, 2 h, and 24 h after irradiation to follow any morphology changes indicative of apoptosis or necrosis.

Initial imaging before irradiation showed very healthy cell growth with good labeling of the cell membrane by IRDye® 700DX anti-EGFR Affibody® in treatments 3-5.

No morphology changes were detected for the control conditions without probe (treatments 1 and 2). At 1 h post irradiation cell rounding and shrinkage was visible in cells of treatment 4, and to a greater extent in cells of treatment 5. The cell surface location of the probe in cells of treatment 3 was different compared to the localization in cells of treatment 4 and 5. In these two treatments, the probe was located in more discrete locations of the cell. The localization of the probe may be due directly or indirectly to the altered cell shape or as a consequence of apoptosis.

At 2 h post irradiation, the cells of treatments 4 and 5 remain rounded and beginning to exhibit blebbing which is a hallmark of apoptosis. The cells of treatment 5 also appear less healthy compared to early time points and to the cells of the other treatments.

At 24 h post irradiation, treatments 1, 2, and 3 all appear normal in appearance. No effect of irradiation (32 J/cm$^2$) was detected in cells that did not receive the probe (treatment 2). Also, no effect of probe on cells without irradiation was detected (treatment 3).

The cells of treatment 4 appear similar in appearance and morphology as at the early time point of 2 h post irradiation. The data suggests that the cells initiated the programmed cell death pathway and did not progress to late apoptosis. Some cells appeared to have normal, healthy morphology, which suggests that the treatment conditions of treatment 4 are sub-lethal.

The cells of treatment 5 which received a higher level of irradiation (32 J/cm$^2$) exhibited complete cell disruption and a dramatic change in morphology that appears similar to that seen in cells treated with IRDye® 700DX labeled antibodies. No healthy cells were observed with these treatments. It should be noted that it takes IRDye® 700DX labeled small molecule probes longer (more time) to kill cells than IRDye® 700DX labeled antibodies. Since apoptosis occurs over a longer time period, it appears that IRDye® 700DX labeled small molecule probes induce apoptosis and IRDye® 700DX labeled antibodies induce necrosis.

To further investigate the subcellular localization of the IRDye® 700DX anti-EGFR Affibody®, we used MitoTracker® Green as described above. A431 cells were plated on glass coverslips in petri-dishes and allowed to equilibrate for 24 h in complete media. The cells were incubated with IRDye® 700DX anti-EGFR Affibody® for 4-5 h, after which cells were irradiated (32 J/cm$^2$). Plates were incubated for an additional 24 h at 37° C. 5% CO$_2$. Cells were treated for 45 min with MitoTracker® Green per manufacturer's instruction. Cells were gently rinsed and incubated for 15 min with DAPI to stain nuclei. Additional rinses were done and the coverslip mounted on glass slides with Fluoromount™ medium. The fluorophores and probe were detected by epi-fluorescence microscopy. The IRDye® 700DX anti-EGFR Affibody® was not located in the mitochondria or the nuclei.

In summary, the example provided herein illustrates the use of IRDye® 700DX labeled small molecule probes for photodynamic therapy. The data shows that the probes are internalized (endocytosed) by the cells, and upon exposure to irradiating light, the cells undergo apoptosis.

Example 10. Induction of Apoptosis by IRDye® 700Dx Small Molecule Conjugate Probes This example illustrates the ability of IRDye® 700DX small molecule conjugates to induce apoptosis in cells, e.g., cancer cells. In this study HTB-186 cells (a desmoplastic cerebellar medulloblastoma cell line) were treated with IRDye® 700DX small molecule conjugates (IRDye® 700DX labeled chlorotoxin, anti-EGFR Affibody®, RGD peptide and EGF ligand). Apoptosis was measured by evaluating caspase 3/7 activity and mitochondrial membrane potential. Apoptosis can be characterized by a variety of cell morphological and biochemical changes including membrane blebbing, cell shrinkage, alteration of membrane asymmetry and permeability, and/or condensation of chromatin and nucleus (Coleman et al., Nat Cell Biol, 2001, 3(4):339-45, Bortner and Cidlowski, Biochem Pharmacol, 1998, 56(12):1549-59; van Engeland et al., Experimental Cell Research, 1997, 235:421-430).

Chlorotoxin (MX) is a scorpion-derived peptide (a 36-amino acid peptide) that can specifically bind to the surface of tumor cells of the brain. The anti-EGFR Affibody® can bind to human EGFR. RBD or arginylglycylaspartic acid is a tripeptide composed of arginine-glycine-aspartic acid. The EGF ligand is a 54 amino acid polypeptide with a molecular weight of about 6:2 kDa.

TABLE 7

Treatment Conditions

| # | Probe | Irradiation |
|---|---|---|
| 1 | Control: No probe | No IRR |
| 2* | Control: No probe | 32 J/cm$^2$ |
| 3* | Control | No IRR |
| 4 | CLTX-700DX | 16 J/cm$^2$ |
| 5 | CLTX-700DX | 32 J/cm$^2$ |
| 6* | 700DX-Affy probe* | 32 J/cm$^2$ |
| 7 | 700DX-RGD (500 nM) | 32 J/cm$^2$ |
| 8 | 700DX-EGF (500 nM) | 32 J/cm$^2$ |

*denotes treatments that are considered negative controls due to technical errors.
Experimental procedure:
(1) Incubate respective treatments with designated probes for about 5 hours at 37° C., 5% CO$_2$.
(2) Cells were rinsed in complete media to remove unbound probe and fresh media added.
(3) Cells were then irradiated to the specific level shown in Table 7 above.
(4) The petri-dishes were incubated overnight at 37° C., 5% CO$_2$.
(5) Cultures were imaged at 20 hours post irradiation and prepared for further analyses: Mitochondrial potential assay (JC-1) and Caspase 3/7 Assay using protocols for the NC-3000 ™ NucleoCounter ® (ChemoMetec A/S; Allerod, Denmark).

In this study a mitochondrial membrane potential assay was performed on cells from treatments 1-8 to determine whether the treated cells underwent apoptosis. The membrane permeant JC-1 dye is commonly used as an indicator of mitochondrial membrane potential in cells. During apoptosis, mitochondria undergo changes, such as changes in the membrane potential, changes to the oxidation-reduction potential of the organelle, and disruption. Mitochondrial membrane potential indicator dyes, such as the fluorescent JC-1 dye are positively charged, and can accumulate in the electronegative interior of mitochondria. As JC-1 dye accumulated in mitochondria, its fluorescence emission shifts from green (about 529 nm) to red (about 590 nm). The presence of red fluorescence due to JC-1 aggregate formation corresponds to regions of high mitochondrial polarization. Depolarized mitochondria are indicated by green fluorescence of the JC-1 monomers. A detectable decrease in the red/green fluorescence intensity ratio indicates mitochondrial depolarization, and thus, apoptosis. In a membrane potential assay, cells are incubated with the JC-1 dye and fluorescence is detected by, for example, flow cytometry, fluorescence microscopy, and fluorescence-based image cytometry.

The caspase 3/7 assay was used to measure caspase 3/7 activity in the cells from the treatments listed above. During apoptosis, caspase enzymes including caspase 3 and 7 are activated and can cleave specific peptide substrates. The caspase 3/7 assay used in this study includes a cell-permeant substrate containing a cleavage site for caspase 3/7. The substrate remains non-fluorescent until caspase 3 or caspase 7 is activated in apoptotic cells. Upon activation, the caspases cleave the substrate, and in turn, a fluorescence signal is emitted. Apoptotic cells with activated caspase 3/7 will fluoresce and cells without activated caspase 3/7 will exhibit minimal or background fluorescence. The fluorescence can be detected by, for example, flow cytometry, fluorescence microscopy, and fluorescence-based image cytometry.

Microscopy images of cells in petri-dishes were captured at 20 h post irradiation. The images were captured in DIC and 700 nm to visualize the probe, and composite images were generated (DIC+700 nm) to visualize the overlay.

The DIC images provide a good representative view of cell health and general growth patterns for comparisons. In the first three treatments (treatments 1-3) little or no difference in overall cell morphology was observed. The cells appeared very healthy. No signal was observed for these treatments in the 700 nm image. We also detect no effect of irradiation (light exposure) on cells untreated with IRDye® 700DX probes (treatment 2).

In Treatments 4 and 5, the CLTX-700DX probes was incubated with the cells and the cells were exposed to either 16 J/cm$^2$ or 32 J/cm$^2$ of light. The cells that received the lower level of irradiation (treatment 4) showed fewer cell morphological changes compared to those receiving the higher level (treatment 5). At the higher irradiation level significantly different morphology patterns were observed. For instance, the cells of treatment 5 had a rounder shape, exhibited cell shrinkage, and appeared to be lifting off the plate. These cells also exhibited a condensed and more discontinuous pattern across the plate.

Treatments 6-8 represent three different IRDye® 700DX-labeled small molecule targeting agents described above. The results of treatment 6 show possible degradation of the 700DX-Affy probe since very little binding of the agent was observed when detecting the 700 nm signals. Alternatively, this may be due to an insufficient concentration of the probe to initiate a cytotoxic effect. This may explain the lack of effect upon irradiation as noted by the healthy appearing cells.

A similar cell morphology was observed in cells treated with 700DX-RGD (treatment 7), 700DX-EGF (treatment 8), and CLTX-700DX (treatment 5). At 20 hours post irradiation, these cells appeared rounded and smaller compared to the cells of the control treatments. In addition, fewer cells were attached to the plate. Also, the probe was detected in the interior of the cells of treatments 5, 7 and 8. The 700 nm images of the cells revealed a punctate pattern. The results show that IRDye® 700DX-labeled small molecule probes are internalized by cells and that upon irradiation, the treated cells undergo cell death.

To determine whether the treated cells are undergoing apoptosis, a caspase 3/7 assay and mitochondrial potential assay were performed. All cells from each treatment were recovered and processed accordingly. Table 8 below provides cells number, % viability, JC-1% shift, and % late apoptotic and dead cells as determined by caspase 3/7 assay.

TABLE 8

Results from caspase 3/7 assay and JC-1 mitochondrial membrane potential assay.

| Treatment # | Probe | Irradiation | Caspase 3 % late apoptotic + dead cells | JC-1 % shift | % Viability | Cell # |
|---|---|---|---|---|---|---|
| 1 | Control: No probe | No IRR | 33 | 34 | 90.3 | 0.7E6 |
| 2* | Control: No probe | 32 J/cm$^2$ | 16 | 29 | 90.7 | 0.7E6 |
| 3* | Control | No IRR | 16 | 30 | 91.0 | 1.0E6 |
| 4 | CLTX-700DX | 16 J/cm$^2$ | 32 | 37 | 88.9 | 0.9E6 |
| 5 | CLTX-700DX | 32 J/cm$^2$ | 59 | 44 | 73.6 | 0.6E6 |
| 6* | 700DX-Affy probe | 32 J/cm$^2$ | 25 | 33 | 90.6 | 0.7E6 |
| 7 | 700DX-RGD (500 nM) | 32 J/cm$^2$ | 57 | 44 | 69.1 | 0.6E6 |
| 8 | 700DX-EGF (500 nM) | 32 J/cm$^2$ | 46 | 42 | 75.7 | 0.7E6 |

*denotes treatments that are considered negative controls due to technical errors.

The cells of treatment 1 appeared morphologically normal and healthy with high cell viability (90.3%). Treatments 2, 3 and 6 were considered controls due to the absence of probe (treatment 2 and 3) or an ineffective probe concentration (treatment 6). These treatments had the highest percentage of viable cells, i.e., greater than 90% viability.

Based on the caspase 3/7 assay, the IRDye® 700DX-labeled small molecules (CLTX-700DX, 700DX-RGD and 700DX-EGF) produced the highest percentage of late apoptosis+dead cells (Treatments 5, 7 and 8). The data also shows that a higher amount of light exposure (32 J/cm$^2$ vs. 16 J/cm$^2$) induced a higher percentage of caspase-3 positive cells (59% vs. 32%) and cells undergoing a JC-1 shift (44% vs. 37%) in cells treated with CLTX-700DX. Similar results were also seen in the cells treated with either 700DX-RGD or 700DX-EGF and exposed to 32 J/cm$^2$. The results show that photodynamic therapy on cells treated with IRDye® 700DX-labeled small molecule probes undergo programmed cell death, i.e., apoptosis.

As described above, a shift in JC-1 signal indicates depolarization of the mitochondria, which signifies that the cell is in an early stage of apoptosis. The data presented in Table 8 show that less than 35% of the cells exhibited a JC-1 shift in the control treatments (treatments 1, 2, 3, and 6). In contrast, at least 37% of the cells receiving an IRDye® 700DX-labeled small molecule probe and irradiated at 16 or 32 J/cm$^2$ exhibited a JC-1 shift. In other words, a higher percentage of cells from treatments 4, 5, 7 and 8 were undergoing apoptosis, as measured by caspase 3/7 activity and mitochondrial membrane potential, than those from the other treatments (treatment 1-3, and 6). In summary, the example illustrates that IRDy® 700DX-labeled small molecule probes are internalized by cells. And upon irradiation, the cell undergo apoptosis, and not necrosis.

Photodynamic treatment (PDT), such as internalization of IRDye 700DX-labeled small molecules followed by irradiation, induces singlet oxygen and superoxide production. This reaction can affect the internal structure of cell, such as the mitochondrial membrane and thus, the mitochondrial membrane potential. In addition, the photodynamic treatment can also induce the activation of caspase proteases. These changes to the treated cells indicated that the photodynamic therapy using small molecule probes can induce apoptosis.

Example 11. Production of Singlet Oxygen

Dyes and conjugated probes (IRDye 700DX carboxylate (700DX), EGF, RGD, and IgG conjugates) were evaluated for production of singlet oxygen using Singlet Oxygen Green Sensor (Life Technologies) and measured by a steady state fluorometer (ex 504 nm/em 525 nm). Controls (water or DMEM medium) and a positive control of methylene blue (MB) were included. Three- to four-fold increases were noted for MB and all 700DX conjugates. When a scavenger of singlet oxygen sodium azide (azide) was added to methylene blue or 700DX a reduction in fluorescence was noted. These data confirm the production of singlet oxygen for 700DX and the conjugates is present after irradiation with appropriate light exposure (690 nm).

Figure 16:
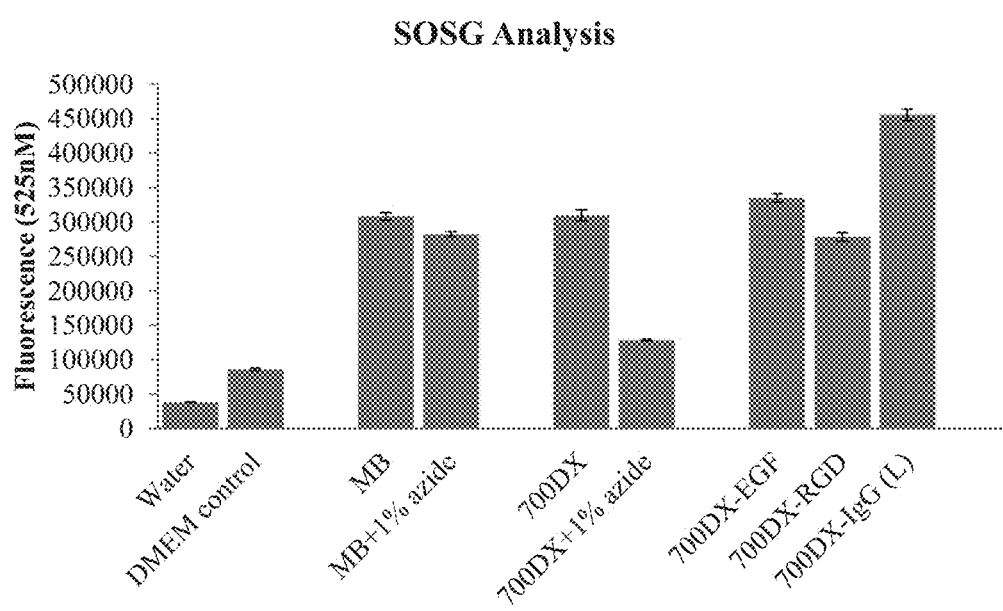
FIG. 16 shows the results of dyes and conjugated probes (IRDye 700DX carboxylate (700DX), EGF, RGD, and IgG conjugates) evaluated for production of singlet oxygen.

Measurements were made every second for 30 sec and averaged. The results are shown in FIG. 16. Solution makeup: SOGS (1 µM), dye or probe addition (10 µM), Tris pH 7.5 (50 uM) and deuterium oxide (50%). Light exposure=32 J/cm$^2$.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

---

Informal Sequence Listing

---

EGF
SEQ ID NO: 1
NSDSECPLSHDGYCLHDGVCMYIEALDKYACNCVVGYIGERC
QYRDLKWWELR

TNFR1 inhibitor peptide
SEQ ID NO: 2
YCWSQYLCY

Vasoactive intestinal peptide
SEQ ID NO: 3
HSDAVFTDNYTRLRKQMAVKKYLNSILN

Bombesin
SEQ ID NO: 4
Pyr-Gln-Arg-Leu-Gly-Asn-Gln-Trp-Ala-Val-
Gly-His-Leu-Met

Substance P
SEQ ID NO: 5
RPKPQQFFGLM

SPARC peptide
SEQ ID NO: 6
CFGIKQKDIDKDLVI octreotide
SEQ ID NO: 7
H-D-Phe-Cys-Phe-D-Trp-Lys-Thr-Cys-Thr(ol)

Exendin-4
SEQ ID NO: 8
HGEGTFTSDLSKQMEEEAVRLFIEWLKNGGPSSGAPPPS-
NH$_2$

SOR-C13
SEQ ID NO: 9
KEFLHPSKVDLPR

SOR-C27
SEQ ID NO: 10
EGKLSSNDTEGGLCKEFLHPSKVDLPR soricidin
SEQ ID NO: 11
DCSQDCAACSILARPAELNTETCILECEGKLSSNDTEGGLC
KEFLHPSKVDLPR Chlorotoxin (CLTX)
SEQ ID NO: 12
MCMPCFTTDHQMARKCDDCCGGKGRGKCYGPQCLCR-NH2

What is claimed is:

1. A method for inducing cytotoxicity by apoptosis in a subject having a disease or condition, the method comprising:
   (a) administering to the subject a therapeutically effective agent comprising a phthalocyanine dye, having a wavelength of 660 to 740 nm, conjugated to a probe that specifically binds to a cell, wherein the bound phthalocyanine dye conjugated probe is internalized into the cell, wherein the probe has a molecular weight of less than 10 kDa and is selected from the group consisting of a peptide, and a small molecule; and
   (b) within 20 minutes to allow internalization of the conjugated probe dye, having a wavelength of 660 to 740 nm, irradiating said cell with an appropriate excitation light in an amount to effectively induce cell death predominately by apoptosis.

2. The method of claim 1, wherein the disease or condition is selected from the group consisting of a vascular disease, cancer, infection due to a bacterial biofilm, an antibiotic-resistant wound infection, actinic keratosis, rosacea, acne, and psoriasis.

3. The method of claim 2, wherein the vascular disease is wet age-related macular degeneration.

4. The method of claim 1, wherein the disease or condition is cancer, which is selected from the group consisting of breast cancer, colorectal cancer, esophageal cancer, lung cancer, prostate cancer, cervical cancer, ovarian cancer, gastric cancer, pancreatic cancer, liver cancer, bladder cancer, brain cancer, head and neck cancer, neuroendocrine cancer, skin cancer, and combinations thereof.

5. The method of claim 1, wherein the subject has a solid tumor or has had a solid tumor.

6. The method of claim 5, wherein the cell is in the solid tumor or the subject's blood.

7. The method of claim 1, wherein the peptide is selected from the group consisting of soricidin, SOR-13 and SOR-C27.

8. The method of claim 1, wherein the small molecule is selected from the group consisting of a VEGFR inhibitor, a TNFR1 inhibitor, a growth factor receptor inhibitor and combinations thereof.

9. The method of claim 1, wherein the probe is a member selected from the group consisting of DTPA-octreotide, [Gluc-Lys]-TOCA, galacto-RGD, AH111585, RGD-K5, FPPRGD2, RP-527, BZH$_3$, [DTPA-Lys$^{40}$]-Exendin-4, and Tc-NT-X1.

10. A method for treating a solid tumor in a subject having cancer, the method comprising:
    (a) administering to the subject a therapeutically effective agent comprising a phthalocyanine dye, having a wavelength of 660 to 740 nm, conjugated to a probe that specifically binds to a cell of the solid tumor, wherein the bound phthalocyanine dye conjugated probe is internalized into the cell, wherein the probe has a molecular weight of less than 10 kDa and is selected from the group consisting of a peptide, and a small molecule; and
    (b) within 20 minutes to allow internalization of the conjugated probe dye, having a wavelength of 660 to 740 nm, irradiating the solid tumor with an appropriate excitation light in an amount to effectively reduce the size of the solid tumor, by inducing cell death predominately by apoptosis.

11. The method of claim 1, wherein the peptide is EGF.

12. The method of claim 1, wherein the peptide is selected from the group consisting of YC-27, cRGDfK, vasoactive intestinal peptide, gastrin-releasing peptide, AH111585, FPPRGD2, PK11195, SPARC, bombesin, substance P, somatostatin, cholecystokinin, glucagon-like peptide-1, neuropeptide Y, octreotide, DOTA-TOC, DOTA-TATE, exendin-4, and combinations thereof.

13. The method of claim 8, wherein the small molecule VEGFR inhibitor is selected from the group consisting of pazopanib, semaxanib, axitinib, cabozantinib, aflibercept, brivanib, tivozanib, ramucirumab, motesanib, vatalanib, cediranib, and combinations thereof.

14. The method of claim 1 or 10, wherein the peptide is chlorotoxin.

15. The method of claim 10, wherein the peptide is EGF.

16. The method of claim 1 or 10, wherein the internalization occurs within 10 minutes.

17. The method of claim 1 or 10, wherein the peptide is RGD.

* * * * *